United States Patent
Marom et al.

(10) Patent No.: US 9,006,188 B2
(45) Date of Patent: Apr. 14, 2015

(54) CO-CRYSTALS OF DAPAGLIFLOZIN

(71) Applicant: Mapi Pharma Ltd., Ness Ziona (IL)

(72) Inventors: Ehud Marom, Kfar Saba (IL); Shai Rubnov, Tel Aviv (IL)

(73) Assignee: Mapi Pharma Ltd., Ness Ziona (IL)

( * ) Notice: Subject to any disclaimer, the term of this patent is extended or adjusted under 35 U.S.C. 154(b) by 0 days.

(21) Appl. No.: 14/286,153

(22) Filed: May 23, 2014

(65) Prior Publication Data

US 2014/0343010 A1 Nov. 20, 2014

Related U.S. Application Data

(63) Continuation of application No. PCT/IL2013/051048, filed on Dec. 23, 2013.

(60) Provisional application No. 61/816,809, filed on Apr. 29, 2013.

(51) Int. Cl.
*A61K 31/70* (2006.01)
*A61K 31/7024* (2006.01)
*A61K 9/14* (2006.01)

(52) U.S. Cl.
CPC ............. *A61K 31/7024* (2013.01); *A61K 9/145* (2013.01)

(58) Field of Classification Search
CPC . A61K 31/351; A61K 31/35; A61K 31/7024; A61K 47/26
See application file for complete search history.

(56) References Cited

U.S. PATENT DOCUMENTS

| | | | |
|---|---|---|---|
| 6,414,126 | B1 | 7/2002 | Ellsworth et al. |
| 6,515,117 | B2 | 2/2003 | Ellsworth et al. |
| 6,936,590 | B2 | 8/2005 | Washburn et al. |
| 7,851,502 | B2 | 12/2010 | Bindra et al. |
| 7,919,598 | B2 | 4/2011 | Gougoutas et al. |
| 8,221,786 | B2 | 7/2012 | Bindra et al. |
| 8,361,972 | B2 | 1/2013 | Bindra et al. |
| 8,501,698 | B2 | 8/2013 | Gougoutas et al. |
| 8,685,934 | B2 | 4/2014 | Strumph et al. |
| 8,716,251 | B2 | 5/2014 | Bindra et al. |

FOREIGN PATENT DOCUMENTS

| | | |
|---|---|---|
| EP | 2597090 A1 | 5/2013 |
| WO | 2004078163 A2 | 9/2004 |
| WO | 2008002824 A1 | 1/2008 |
| WO | 2011060290 A2 | 5/2011 |
| WO | 2013064909 A2 | 5/2013 |

OTHER PUBLICATIONS

Andre S. Raw (2003) Regulatory Considerations on Pharmaceutical Solids: Polymorphs/Salts and Co-Crystals. Dec. 31, 2003, slides 28-43.
Written Opinion and International Search Report issued in International Patent Appln. No. PCT/IL2013/051048 on Mar. 13, 2014, 20 pages.
BMS-AstraZeneca Dapagliflozin Diabetes Drug Falls Short; Pfizer's Answer on the Horizon? Posted by See Arr Oh on Jul. 29, 2011. Retrieved on Sep. 29, 2014 http://cenblog.org/the-haystack/2011/07/bms-astrazeneca-dapagliflozin-diabetes-drug-falls-short-pfizer%E2%80%99s-answer-on-the-horizon/.
Dapagliflozin Sees Light, from New Drug Approvals. Posted by Anthony Melvin Crasto on Dec. 18, 2013. Retrieved on Sep. 29, 2014 http://newdrugapprovals.org/2013/12/18/dapagliflozin-sees-light/.
Dapagliflozin, from Organic Spectroscopy International. Posted by Anthony Melvin Crasto Jan. 10, 2014. Retrieved on Sep. 29, 2014 http://orgspectroscopyint.blogspot.co.il/search?q=dapagliflozin.
Miao et al., (2013) Pharmacokinetics, metabolism, and excretion of the antidiabetic agent ertugliflozin (PF-04971729) in healthy male subjects. Drug Metab Dispos 41: 445-56.
Zhang et al., (2011) EGT1442, a potent and selective SGLT2 inhibitor, attenuates blood glucose and HbA(1c) levels in db/db mice and prolongs the survival of stroke-prone rats. Pharmacol Res 63: 284-93.

*Primary Examiner* — Elli Peselev
(74) *Attorney, Agent, or Firm* — Rothwell, Figg, Ernst & Manbeck, P.C.

(57) ABSTRACT

The present invention provides novel co-crystal forms of dapagliflozin, namely a dapagliflozin lactose co-crystal and a dapagliflozin asparagine co-crystal, to pharmaceutical compositions comprising same, methods for their preparation and uses thereof for treating type 2 diabetes.

15 Claims, 24 Drawing Sheets

CO-CRYSTALS OF DAPAGLIFLOZIN

CROSS REFERENCE TO RELATED APPLICATIONS

The present application is a continuation application of International Application No.: PCT/IL2013/051048, with an international filing date of Dec. 23, 2013, which claims the benefit of U.S. Provisional Application No. 61/816,809 filed on Apr. 29, 2013, which are incorporated herein in their entireties.

FIELD OF THE INVENTION

The present invention relates to novel crystalline forms of dapagliflozin, namely a dapagliflozin lactose co-crystal and a dapagliflozin asparagine co-crystal, to pharmaceutical compositions comprising same, methods for their preparation and uses thereof for treating type 2 diabetes.

BACKGROUND OF THE INVENTION

Diabetes mellitus type 2 or type 2 diabetes (formerly called non-insulin-dependent diabetes mellitus (NIDDM), or adult-onset diabetes) is a disorder that is characterized by high blood glucose in the context of insulin resistance and relative insulin deficiency. While it is often initially managed by increasing exercise and dietary modifications, medications are typically needed as the disease progresses. There are an estimated 23.6 million people in the U.S. (7.8% of the population) with diabetes, 90% of whom are type 2. Worldwide, it is estimated that at least 171 million people suffer from type 2 diabetes. With prevalence rates doubling between 1990 and 2005, CDC has characterized the increase as an epidemic. In addition, while traditionally considered a disease of adults, type 2 diabetes is increasingly diagnosed in children in parallel to rising obesity rates due to alterations in dietary patterns as well as in life styles during childhood.

Hyperglycemia plays an important role in the pathogenesis of type 2 diabetes by means of glucotoxicity. Thus, effective glycemic control not only reduces the incidence of microvascular complications but also corrects the metabolic abnormalities that contribute to the progression of the disease. Plasma glucose is normally filtered in the kidney in the glomerulus and actively reabsorbed in the proximal tubule. The sodium dependent glucose transporter (SGLT2) appears to be the major transporter responsible for the reuptake of glucose at this site. Thus, a selective inhibitor of SGLT2 in the kidney is expected to normalize plasma glucose levels by enhancing the excretion of glucose in the urine, thereby improving insulin sensitivity, and delaying the development of diabetic complications, in the absence of significant gastrointestinal side effects.

Dapagliflozin is an orally active SGLT2 inhibitor that is disclosed in U.S. Pat. No. 6,515,117.

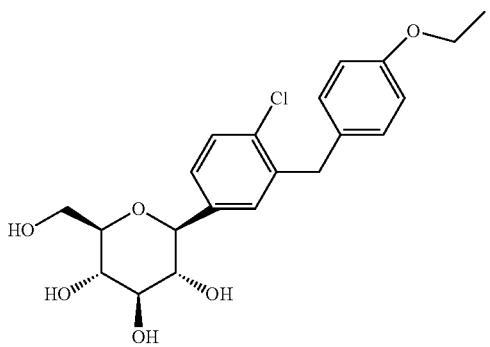 [SMILES: CCOc1ccc(Cc2cc([C@@H]3O[C@H](CO)[C@@H](O)[C@H](O)[C@H]3O)ccc2Cl)cc1]

U.S. Pat. No. 6,515,117 describes the synthesis of dapagliflozin from the corresponding tetraacetylated β-C-glucoside precursor. After removal of the acetate moieties, the residue was dissolved in EtOAc, washed with brine containing $KHSO_4$ and dried. The volatile solvents were removed and the resultant oil in a minimum amount of $CH_2Cl_2$ was foamed under vacuum to give the desired title compound described as a glassy off white solid containing 0.11 mol % of EtOAc.

A new crystalline or amorphous form of a compound may possess physical properties that differ from, and are advantageous over, those of other crystalline or amorphous forms. These include, packing properties such as molar volume, density and hygroscopicity; thermodynamic properties such as melting temperature, vapor pressure and solubility; kinetic properties such as dissolution rate and stability under various storage conditions; surface properties such as surface area, wettability, interfacial tension and shape; mechanical properties such as hardness, tensile strength, compactibility, handling, flow and blend; and filtration properties. Variations in any one of these properties may affect the chemical and pharmaceutical processing of a compound as well as its bioavailability and may often render the new form advantageous for pharmaceutical and medical use.

PCT International Patent Publication No. WO 2008/002824 discloses crystalline solvates and complexes of dapagliflozin, namely (S)-propylene glycol ((S)-PG) hydrate (Form SC-3), (R)-propylene glycol ((R)-PG) hydrate (Form SD-3), EtOH dihydrate (Form SA-I), ethylene glycol (EG) dihydrate (Form SB-I), ethylene glycol (EG) dihydrate (Form SB-2), 1:2 L-proline complex (Form 3), 1:1 L-proline complex (Form 6), 1:1 L-proline hemihydrate complex (Form H.5-2), and 1:1 L-phenylalanine complex (Form 2).

U.S. Pat. Nos. 7,851,502 and 8,221,786 disclose pharmaceutical compositions comprising dapagliflozin propylene glycol (PG) hydrate.

There still remains an unmet need for solid state forms of dapagliflozin having good physicochemical properties, desirable bioavailability, and advantageous pharmaceutical parameters.

SUMMARY OF THE INVENTION

The present invention provides new crystalline forms of dapagliflozin, namely a dapagliflozin lactose co-crystal and a dapagliflozin asparagine co-crystal, pharmaceutical compositions comprising these forms, methods for their preparation and uses thereof for treating type 2 diabetes.

The present invention is based in part on the unexpected finding that the new forms disclosed herein possess advantageous physicochemical properties which render their processing as medicaments beneficial. The applicants of the present invention have characterized the dapagliflozin form described in U.S. Pat. No. 6,515,117 as being amorphous and unstable (very hygroscopic, readily forming a gel-like consistency). Accordingly, this form appears unsuitable for pharmaceutical applications. In contrast, the new co-crystal forms of the present invention have adequate stability characteristics enabling their incorporation into a variety of different formulations particularly suitable for pharmaceutical utility.

According to one aspect, the present invention provides a dapagliflozin lactose co-crystal. In some embodiments, the dapagliflozin lactose co-crystal is characterized by an X-ray powder diffraction pattern substantially as shown in FIG. 1A or FIG. 1B. Each possibility represents a separate embodiment of the present invention.

In another embodiment, the dapagliflozin lactose co-crystal of the present invention is further characterized by a Differential Scanning Calorimetry (DSC) profile substantially as shown in FIG. 2. In another embodiment, the dapagliflozin lactose co-crystal of the present invention is further characterized by a Polarized Light Microscope (PLM) profile substantially as shown in FIG. 3A. In another embodiment, the dapagliflozin lactose co-crystal of the present invention is further characterized by a Thermogravimetric Analysis (TGA) profile substantially as shown in FIG. 4. In another embodiment, the dapagliflozin lactose co-crystal of the present invention is further characterized by a $^1$H-NMR profile substantially as shown in FIG. 5. In another embodiment, the dapagliflozin lactose co-crystal of the present invention is further characterized by a Dynamic Vapor Sorption (DVS) profile substantially as shown in FIGS. 6A and 6B. Each possibility represents a separate embodiment of the present invention.

According to another aspect, the present invention provides a dapagliflozin asparagine co-crystal. In some embodiments, the dapagliflozin asparagine co-crystal is characterized by an X-ray powder diffraction pattern substantially as shown in FIG. 7A or FIG. 7B. Each possibility represents a separate embodiment of the present invention.

In another embodiment, the dapagliflozin asparagine co-crystal of the present invention is further characterized by a DSC profile substantially as shown in FIG. 8. In another embodiment, the dapagliflozin asparagine co-crystal of the present invention is further characterized by a PLM profile substantially as shown in FIG. 9A. In another embodiment, the dapagliflozin asparagine co-crystal of the present invention is further characterized by a TGA profile substantially as shown in FIG. 10. In another embodiment, the dapagliflozin asparagine co-crystal of the present invention is further characterized by a $^1$H-NMR profile substantially as shown in FIG. 11. In another embodiment, the dapagliflozin asparagine co-crystal of the present invention is further characterized by a DVS profile substantially as shown in FIGS. 12A and 12B. Each possibility represents a separate embodiment of the present invention.

In one embodiment, the present invention provides a process for preparing the dapagliflozin co-crystals of the present invention, the process comprising the steps of: mixing dapagliflozin with lactose or asparagine at about a 1:1 molar ratio in an organic solvent, and precipitating the co-crystal. In some embodiments, the organic solvent is a $C_1$-$C_4$ alcohol, preferably isopropanol.

In certain embodiments, the present invention provides a pharmaceutical composition comprising the dapagliflozin lactose co-crystal of the present invention as an active ingredient, and a pharmaceutically acceptable carrier. In other embodiments, the present invention provides a pharmaceutical composition comprising the dapagliflozin asparagine co-crystal of the present invention as an active ingredient, and a pharmaceutically acceptable carrier. Each possibility represents a separate embodiment of the present invention.

In a particular embodiment, the pharmaceutical composition is in the form of a tablet, a capsule, a pill, a powder or a solution. In another particular embodiment, the pharmaceutical composition is in the form of a sublingual tablet, an orally disintegrating tablet or an orally disintegrating wafer. Each possibility represents a separate embodiment of the present invention.

In some embodiments, the crystalline dapagliflozin co-crystals of the present invention are useful for treating type 2 diabetes. Thus, in various embodiments, the present invention provides a pharmaceutical composition comprising the dapagliflozin lactose or asparagine co-crystal of the present invention as an active ingredient, and a pharmaceutically acceptable carrier for use in treating or preventing type 2 diabetes. Each possibility represents a separate embodiment of the present invention.

In some embodiments, the present invention provides a method of treating or preventing type 2 diabetes, comprising administering to a subject in need thereof an effective amount of any of the dapagliflozin lactose or asparagine co-crystal of the present invention, or a pharmaceutical composition comprising either co-crystal. Each possibility represents a separate embodiment of the present invention.

In additional embodiments, the present invention provides the use of an effective amount of any of the dapagliflozin lactose or asparagine co-crystals of the present invention, or a pharmaceutical composition comprising either of these polymorphic forms, for the manufacture of a medicament for treating type 2 diabetes. Each possibility represents a separate embodiment of the present invention.

In other embodiments, the subject is a mammal, such as a human.

Further embodiments and the full scope of applicability of the present invention will become apparent from the detailed description given hereinafter. However, it should be understood that the detailed description and examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1A: dapagliflozin lactose co-crystal (B) compared with dapagliflozin free form (amorphous) (A); lactose (C); and physical mixture of lactose with dapagliflozin (D). FIG. 1B: dapagliflozin lactose co-crystal before (A) and after (B) DVS test.

FIG. 6A: DVS isotherm plot. FIG. 6B: DVS change in mass (ref) plot.

FIG. 7A: dapagliflozin asparagine co-crystal (B) compared with dapagliflozin free form (amorphous) (A); asparagine (C), and physical mixture of asparagine with dapagliflozin (D) FIG. 7B: dapagliflozin asparagine co-crystal before (A) and after (B) DVS test.

FIG. 12A: DVS isotherm plot. FIG. 12B: DVS change in mass (ref) plot.

FIG. 18A: DVS change in mass (ref) plot FIG. 18B: DVS isotherm plot.

DETAILED DESCRIPTION OF THE INVENTION

Figure 1A:
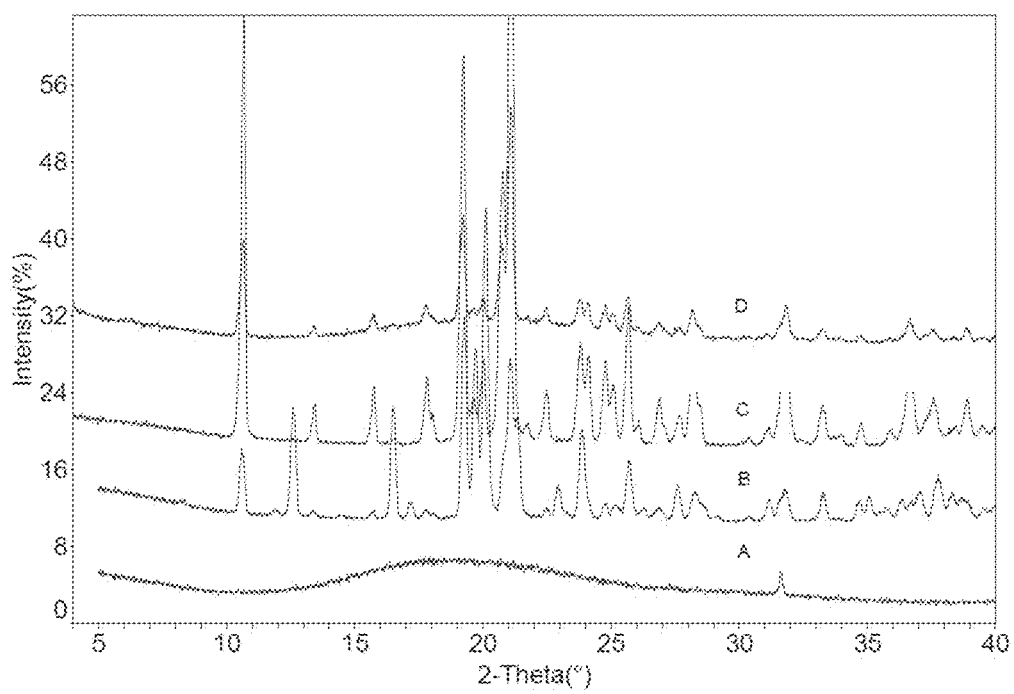
FIGS. 1A and 1B illustrate a characteristic X-ray diffraction pattern of a dapagliflozin lactose co-crystal according to the present invention.

The present invention is directed to two novel crystalline forms of (2S,3R,4R,5S,6R)-2-[4-chloro-3-(4-ethoxybenzyl) phenyl]-6-(hydroxymethyl)tetrahydro-2H-pyran-3,4,5-triol (dapagliflozin), which comprise dapagliflozin co-crystallized with lactose or asparagine. These forms are designated herein "dapagliflozin lactose co-crystal" and "dapagliflozin asparagine co-crystal", respectively. These novel polymorphic forms are different from and advantageous over the amorphous and crystalline dapagliflozin forms described in the prior art.

The present invention is further directed to pharmaceutical compositions comprising the crystalline dapagliflozin co-crystal forms of the present invention and a pharmaceutically acceptable carrier and their use in treating conditions and disorders for which dapagliflozin is therapeutically effective, for example type 2 diabetes.

The present invention is further directed to methods of preparing the novel dapagliflozin crystalline forms of the present invention.

The term "co-crystal" means a crystalline material comprised of two or more unique solids at room temperature, each containing distinctive physical characteristics, such as structure, melting point and heats of fusion. In the context of the present invention, the term "co-crystal" means a crystalline material comprised of dapagliflozin and a second solid molecule (designated "co-crystal former"). In one preferred embodiment, the co-crystal former is lactose. In another preferred embodiment, the co-crystal former is asparagine. The stoichiometry of each component in the co-crystal can vary. In some embodiments, the stoichiometry of the complex is 1:1, i.e., one molecule of dapagliflozin co-crystallized with one molecule of lactose or asparagine. In other embodiments, one molecule of dapagliflozin co-crystallizes with more than one molecule of lactose or asparagine, such that the stoichiometry between the two molecules is, e.g., 1:2, 1:3, 1:4 etc. dapagliflozin:lactose/asparagine. In other embodiments, one molecule of dapagliflozin co-crystallizes with less than one molecule of lactose or asparagine, such that the stoichiometry between the two molecules is, e.g., 4:1, 3:1, 2:1 etc. dapagliflozin:lactose/asparagine. The term "co-crystal" does not encompass a physical mixture of dapagliflozin with lactose or asparagine. Also included in the present invention are solvates and hydrates (e.g., monohydrate, dihydrate etc.) as well as anhydrous and various polymorphic forms of the co-crystals of the present invention, and salts thereof.

It has surprisingly been found that when an active pharmaceutical ingredient (API) and a selected co-crystal former are allowed to form co-crystals, the resulting co-crystals give rise to improved properties of the API, as compared to the API in a free form particularly with respect to at least one of the following parameters: solubility, dissolution, bioavailability, stability, Cmax, Tmax, processability, longer lasting therapeutic plasma concentration, hygroscopicity, crystallization of amorphous compounds, decrease in form diversity (including polymorphism and crystal habit), change in morphology or crystal habit, etc. For example, a co-crystal form of an API is particularly advantageous where the original API is insoluble or sparingly soluble in water. Additionally, the co-crystal properties conferred upon the API are also useful because the bioavailability and the plasma concentration and/ or serum concentration of the API can be improved. This is particularly advantageous for orally-administrable formulations. Moreover, the dose response of the API can be improved, for example by increasing the maximum attainable response and/or increasing the potency of the API by increasing the biological activity per dosing equivalent.

The novel co-crystal forms of dapagliflozin disclosed herein possess improved physicochemical properties including high stability and lower hygroscopicity as compared with the free (amorphous) form known in the art.

Dapagliflozin Lactose Co-Crystal

Provided herein is a co-crystal of dapagliflozin with lactose (herein "dapagliflozin lactose co-crystal") which is characterized by a unique X-ray diffraction pattern. Characteristic X-ray diffraction patterns can be seen in FIGS. 1A and B. As seen in FIG. 1A, the X-ray diffraction pattern of the co-crystal is different from that of a physical mixture of lactose with dapagliflozin, lactose alone or dapagliflozin free form (amorphous), demonstrating that this is a novel co-crystalline form.

The dapagliflozin lactose co-crystal of the present invention can be further characterized by its melting point and by using various techniques including, but not limited to, thermal analysis (e.g. thermogravimetric analysis (TGA) and differential scanning calorimetry (DSC)), Polarized Light Microscopy (PLM), and Nuclear Magnetic Resonance (NMR). Hygroscopicity of the new co-crystalline form is measured by Dynamic vapor sorption (DVS).

Figure 2:
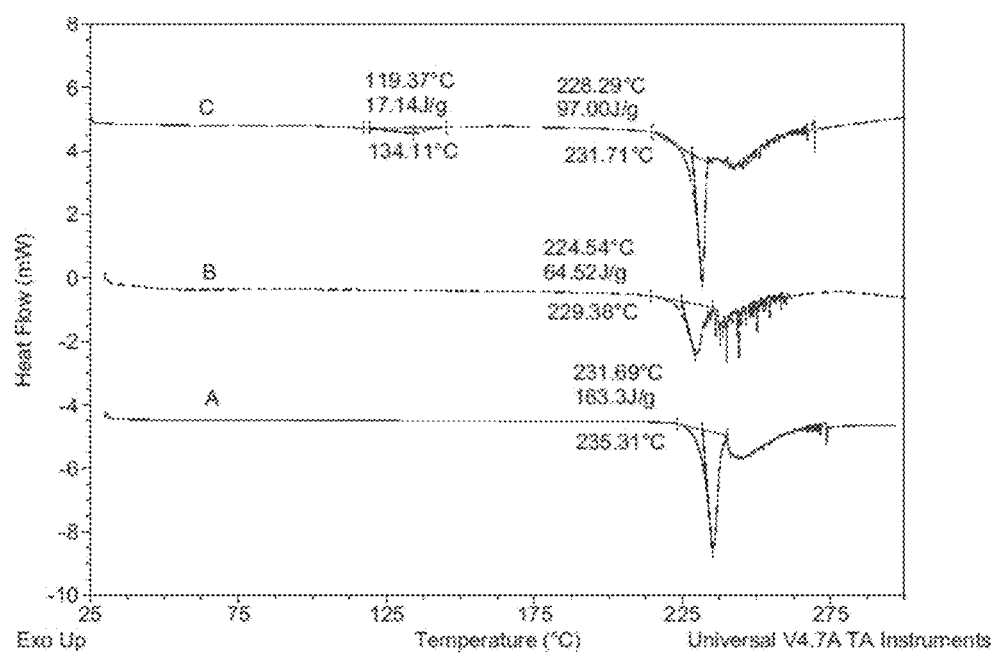
FIG. 2 illustrates a characteristic DSC profile of a dapagliflozin lactose co-crystal according to the present invention (C). Also shown in comparison are the DSC patterns of lactose (A) and of a physical mixture of lactose with dapagliflozin (B).

In certain embodiments, the dapagliflozin lactose co-crystal of the present invention is characterized by a DSC profile substantially as shown in FIG. 2 with a major peak at about 231.7° C. (onset at about 228.3° C.), and with a minor peak (shoulder) at about 134.1° C. (onset at about 119.4° C.). As seen, the DSC profile of the co-crystal is different from that of a physical mixture of dapagliflozin and lactose.

Figure 3A:
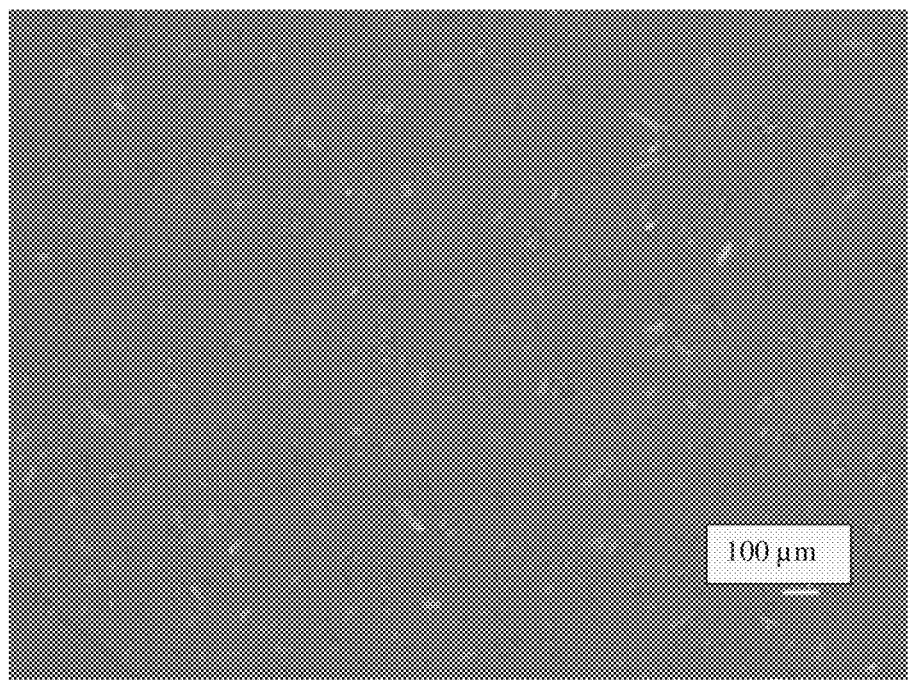
FIGS. 3A and 3B illustrate a characteristic PLM spectrum of a dapagliflozin lactose co-crystal according to the present invention (FIG. 3A) and a physical mixture of lactose with dapagliflozin (FIG. 3B) (20×PL).
Figure 3B:
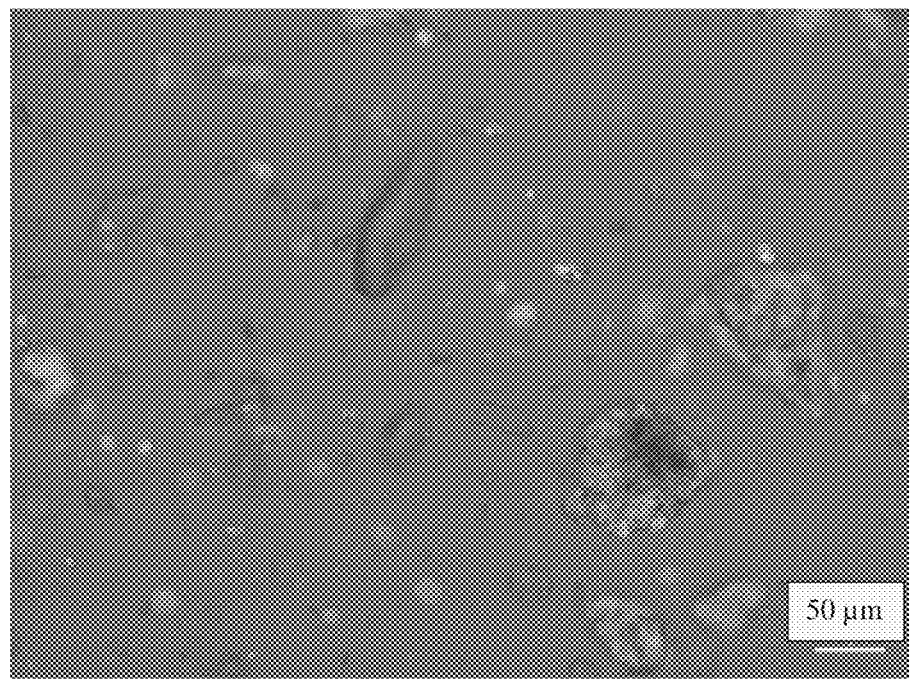

In other embodiments, the dapagliflozin lactose co-crystal is further characterized by a PLM spectrum substantially as shown in FIG. 3A. By way of comparison, FIG. 3B shows the PLM spectrum of a physical mixture of lactose with dapagliflozin.

Figure 4:
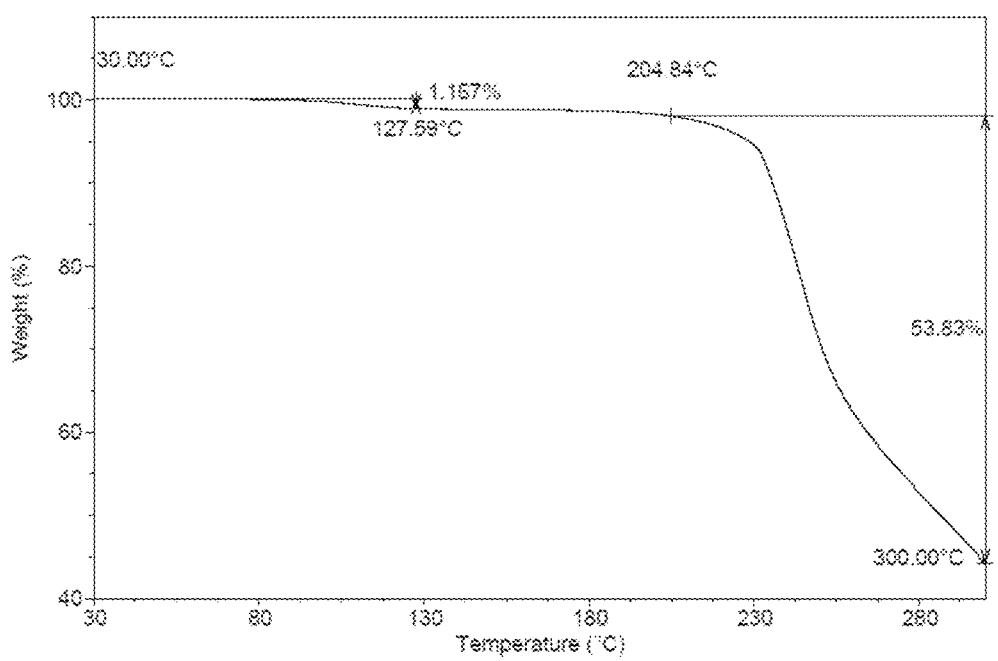
FIG. 4 illustrates a characteristic TGA profile of a dapagliflozin lactose co-crystal according to the present invention.

In other embodiments, the dapagliflozin lactose co-crystal is further characterized by a TGA profile substantially as shown in FIG. 4.

Figure 5:
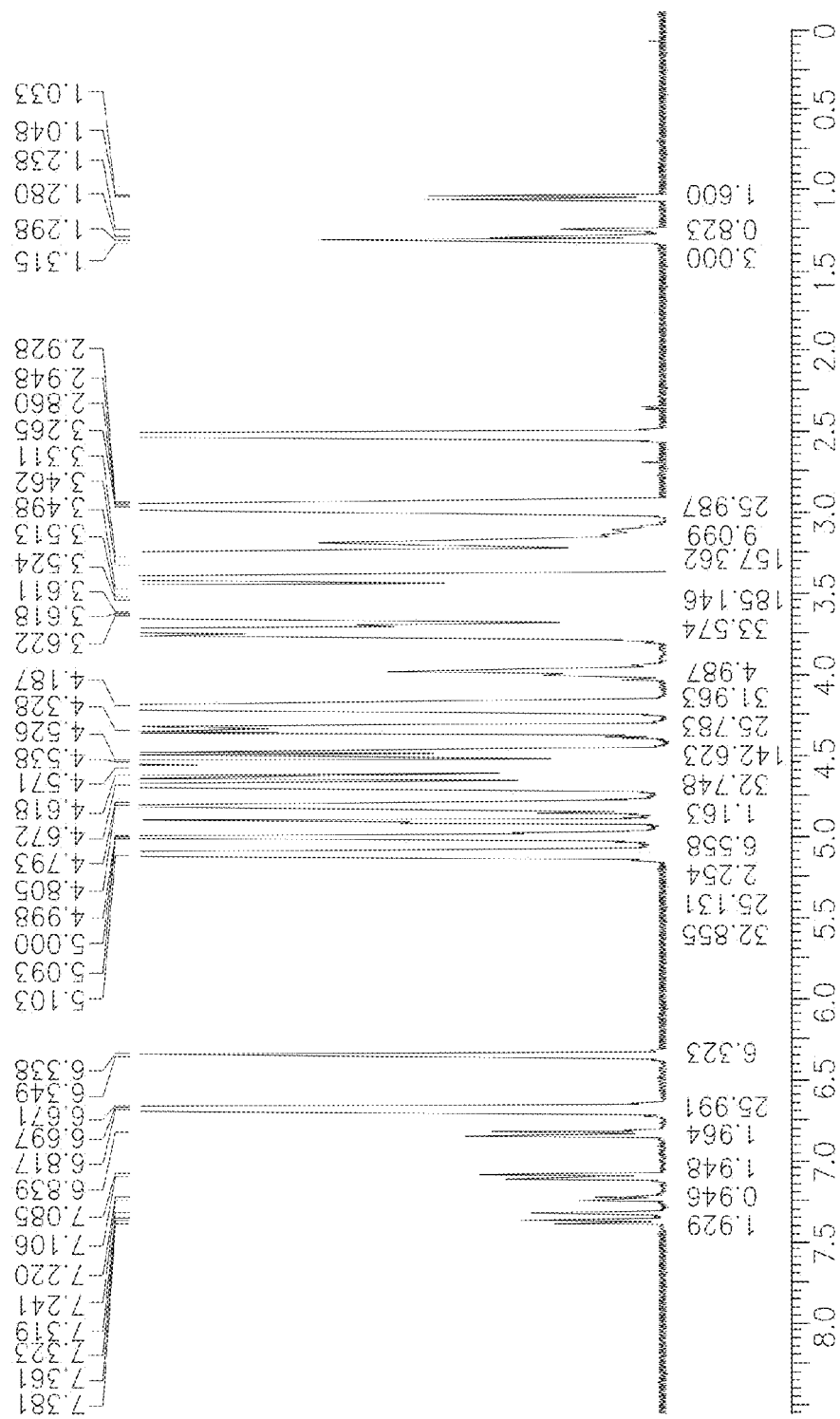
FIG. 5 illustrates a characteristic $^1$H-NMR spectrum of a dapagliflozin lactose co-crystal according to the present invention.

In other embodiments, the dapagliflozin lactose co-crystal is characterized by an $^1$H NMR spectrum substantially as shown in FIG. 5.

Figure 6A:
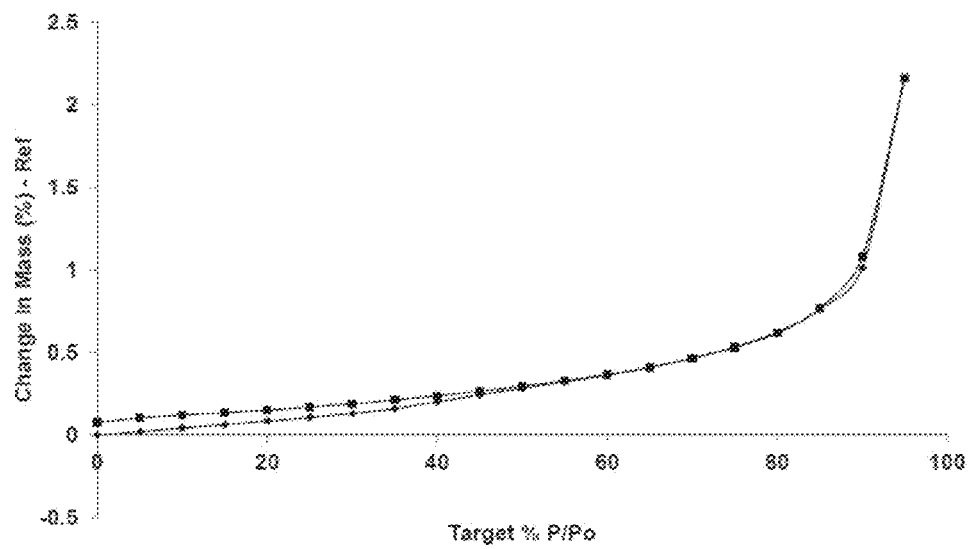
FIGS. 6A and 6B illustrate a characteristic DVS spectrum of a dapagliflozin lactose co-crystal according to the present invention.
Figure 6B:
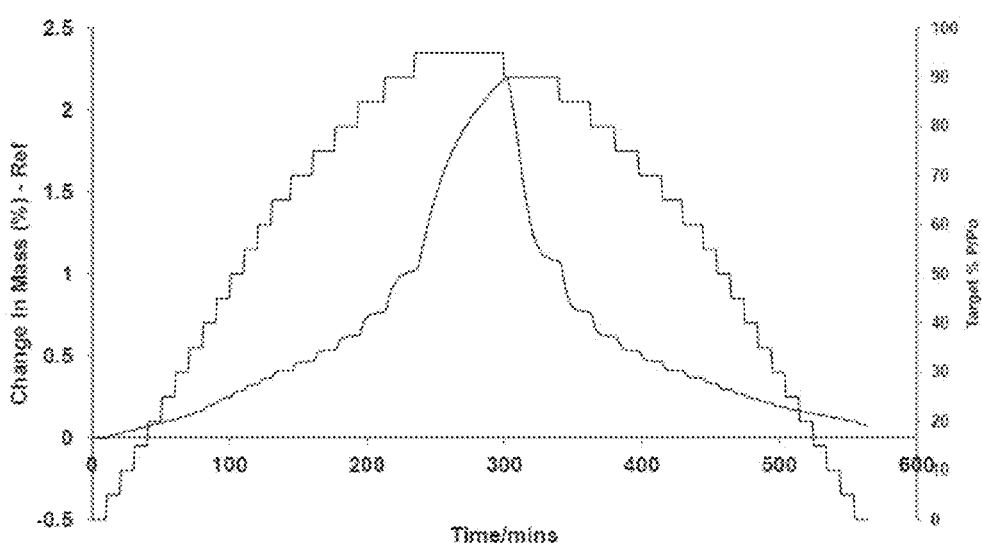

In other embodiments, the dapagliflozin lactose co-crystal is characterized by a DVS spectrum substantially as shown in FIG. 6. FIG. 6A shows the DVS isotherm plot, and FIG. 6B shows the DVS change in mass.

The present invention further provides a process for the preparation of the dapagliflozin lactose co-crystal of the present invention. The process comprises (a) mixing dapagliflozin with lactose, preferably at about a 1:1 molar ratio in an organic solvent; and (b) precipitating the co-crystal. Any type of organic solvent can be used in this process. Preferred solvents are lower alkyl alcohols (e.g., a $C_1$-$C_6$ alcohol). A currently preferred solvent is isopropanol. Other suitable alcohols include, but are not limited to, methanol, ethanol, propanol, butanol, cyclohexanol and the like.

Any dapagliflozin can be used as the starting material in the process of the present invention. In one embodiment, a dapagliflozin free form (amorphous) as described in U.S. Pat. No. 6,515,117 is used as the starting material for preparing the co-crystals of the present invention. The process of the present invention can also use as the starting material any other dapagliflozin known in the art, for example the dapagliflozin described in WO 2008/002824, U.S. Pat. No. 7,851,502 and U.S. Pat. No. 8,221,786. The contents of each of these references are incorporated by reference in their entirety herein.

Dapagliflozin Asparagine Co-Crystal

Figure 7A:
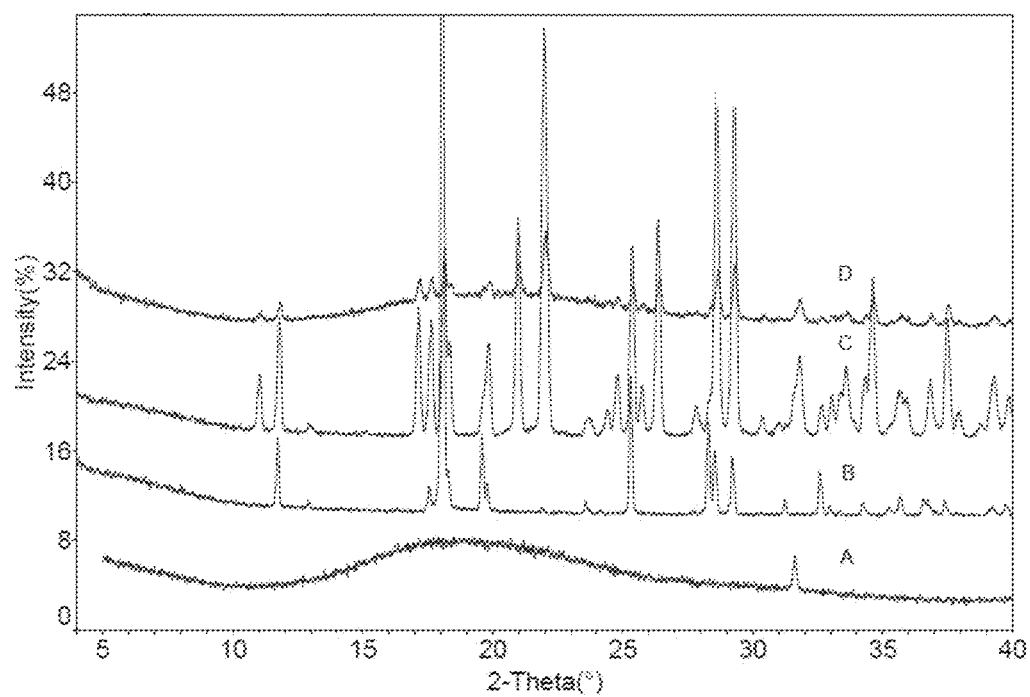
FIGS. 7A and 7B illustrate a characteristic X-ray diffraction pattern of a dapagliflozin asparagine co-crystal according to the present invention.

Provided herein is a co-crystal of dapagliflozin with asparagine (herein "dapagliflozin asparagine co-crystal") which is characterized by a unique X-ray diffraction pattern. Characteristic X-ray diffraction patterns can be seen in FIGS. 7A and B. As seen in FIG. 7A, the X-ray diffraction pattern of the co-crystal is different from that of a physical mixture of asparagine with dapagliflozin, asparagine alone or dapagliflozin free form (amorphous), demonstrating that this is a novel co-crystalline form.

The dapagliflozin asparagine co-crystal of the present invention can be further characterized by its melting point and by using various techniques including, but not limited to, thermal analysis (e.g. TGA DSC), PLM, and NMR. Hygroscopicity of the new crystalline form is measured by DVS.

Figure 8:
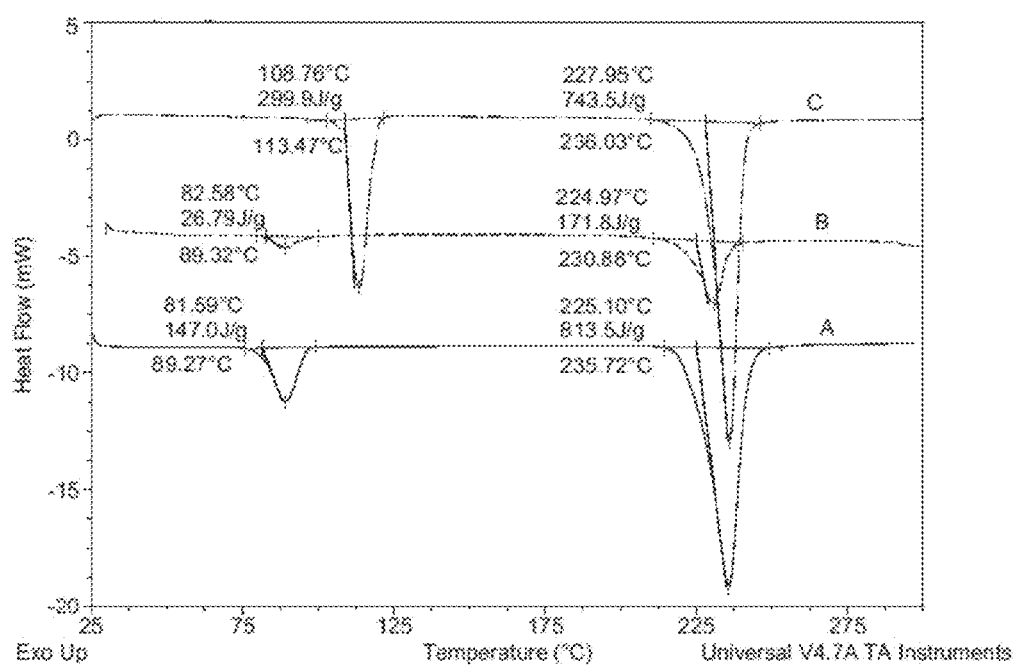
FIG. 8 illustrates a characteristic DSC profile of a dapagliflozin asparagine co-crystal according to the present invention (C). Also shown in comparison are the DSC patterns of asparagine (A) and of a physical mixture of asparagine with dapagliflozin (B).

In certain embodiments, the dapagliflozin asparagine co-crystal of the present invention is characterized by a DSC profile substantially as shown in FIG. 8 with a major peak at about 236.0° C. (onset at about 228.0° C.), and with a minor peak (shoulder) at about 113.5° C. (onset at about 108.8° C.). As seen, the DSC profile of the co-crystal is different from that of a physical mixture of dapagliflozin and asparagine.

Figure 9A:
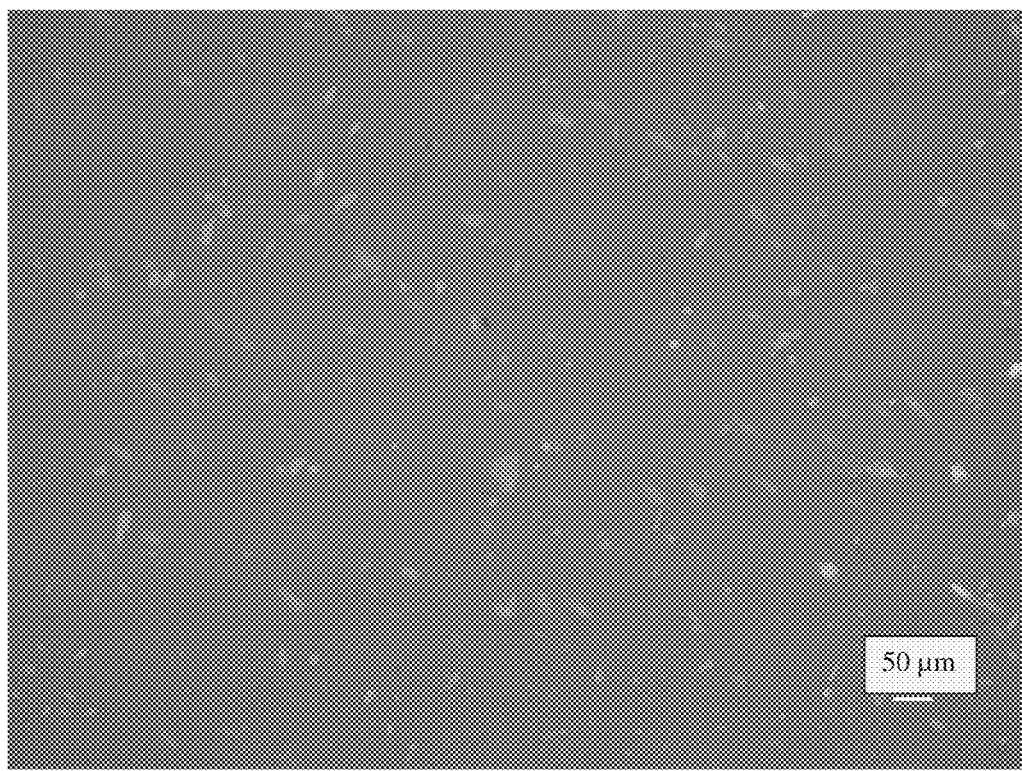
FIGS. 9A and 9B illustrate a characteristic PLM spectrum of a dapagliflozin asparagine co-crystal according to the present invention (FIG. 9A) and a physical mixture of asparagine with dapagliflozin (FIG. 9B) (10×PL).
Figure 9B:
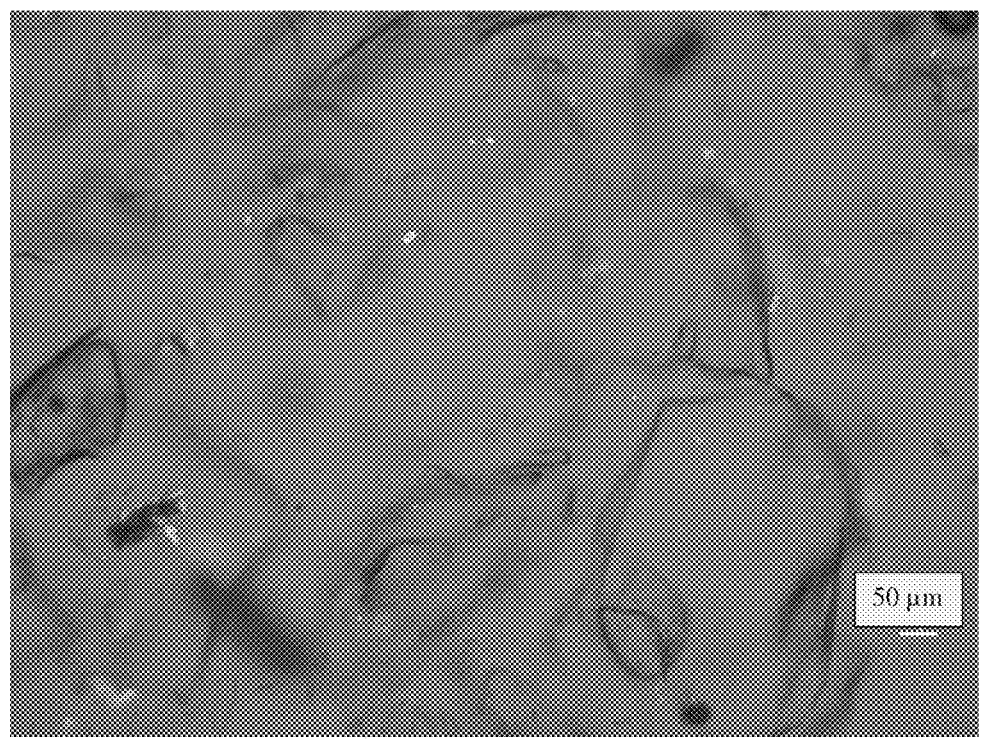

In other embodiments, the dapagliflozin asparagine co-crystal is further characterized by a PLM spectrum substantially as shown in FIG. 9A. By way of comparison, FIG. 9B shows the PLM spectrum of a physical mixture of asparagine with Dapagliflozin.

Figure 10:
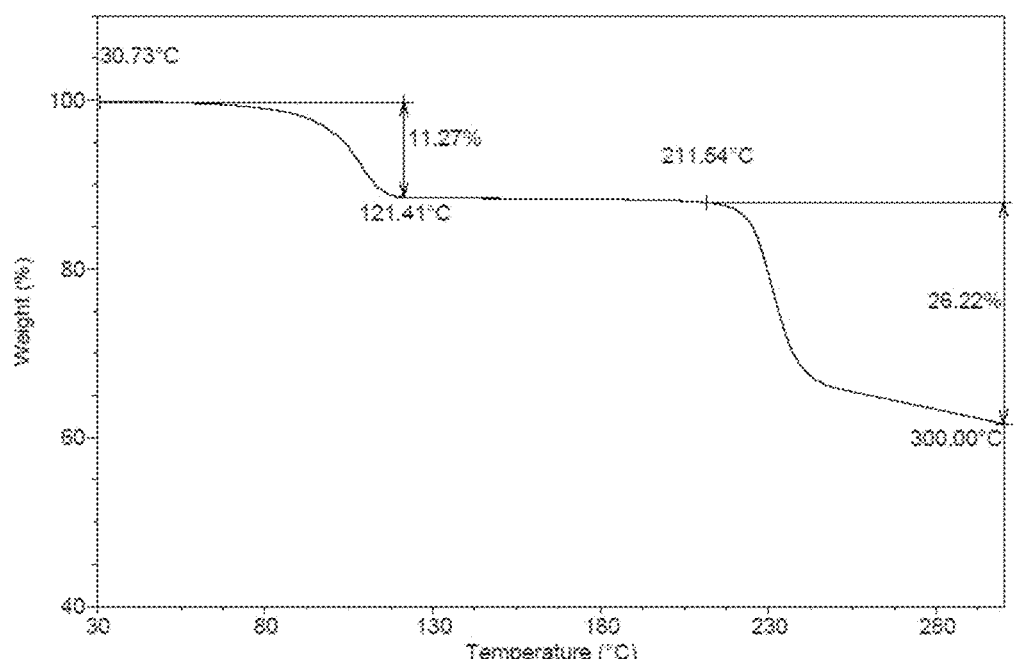
FIG. 10 illustrates a characteristic TGA profile of a dapagliflozin asparagine co-crystal according to the present invention.

In other embodiments, the dapagliflozin asparagine co-crystal is further characterized by a TGA profile substantially as shown in FIG. 10.

Figure 11:
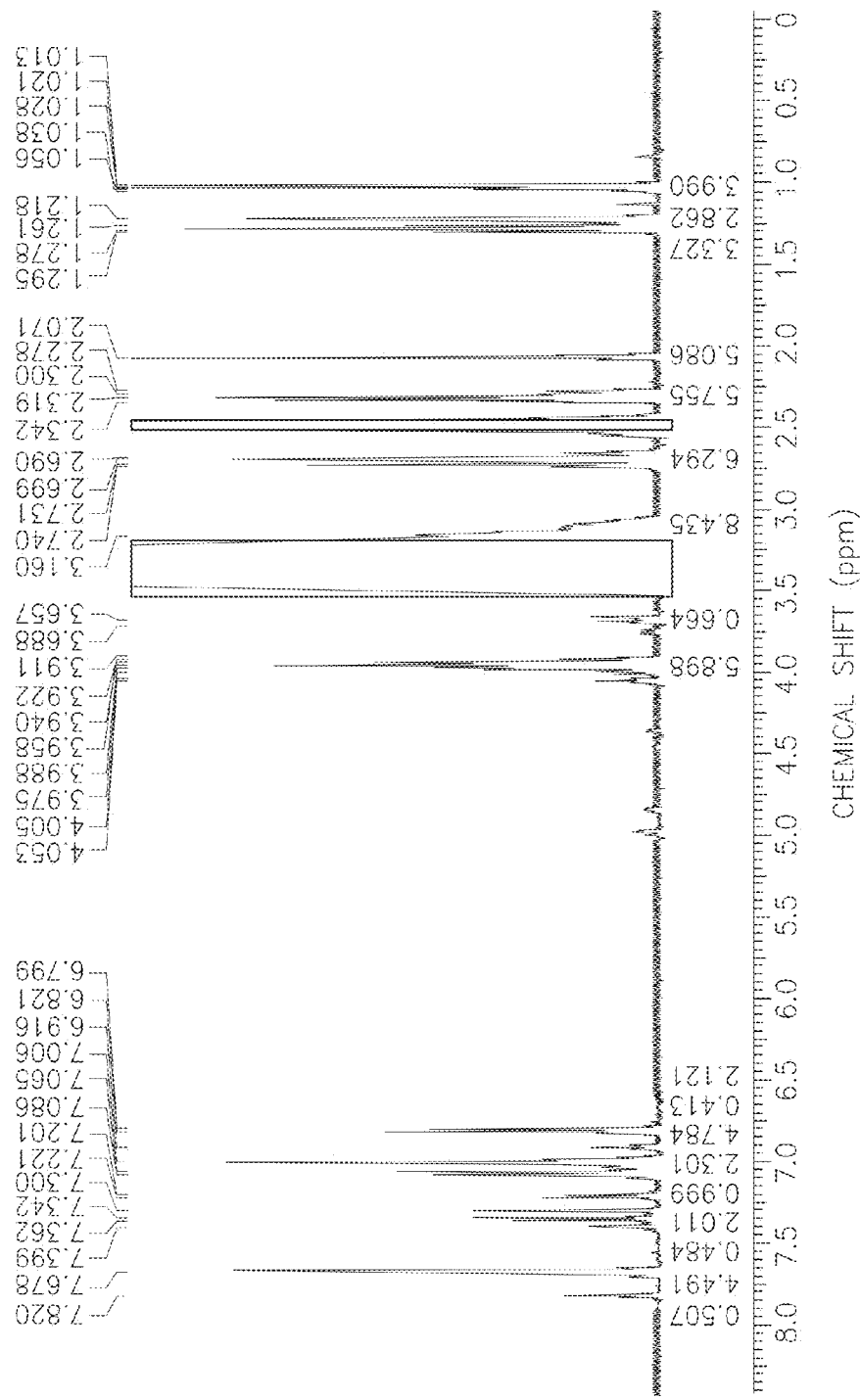
FIG. 11 illustrates a characteristic $^1$H-NMR spectrum of a dapagliflozin asparagine co-crystal according to the present invention.

In other embodiments, the dapagliflozin asparagine co-crystal is characterized by an $^1$H NMR spectrum substantially as shown in FIG. 11.

Figure 12A:
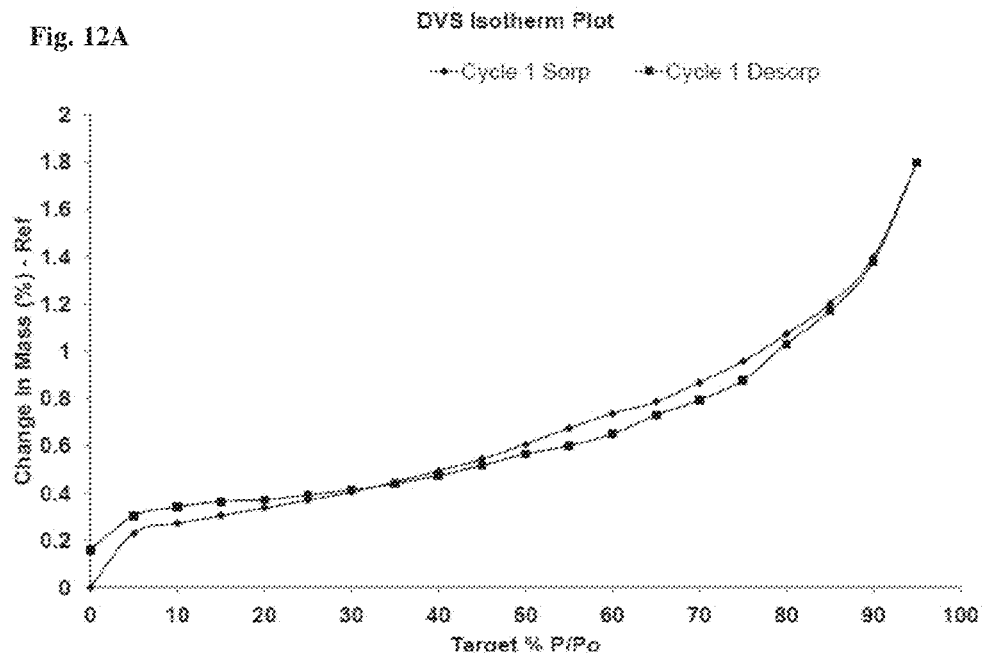
FIGS. 12A and 12B illustrate a characteristic DVS spectrum of a dapagliflozin asparagine co-crystal according to the present invention.
Figure 12B:
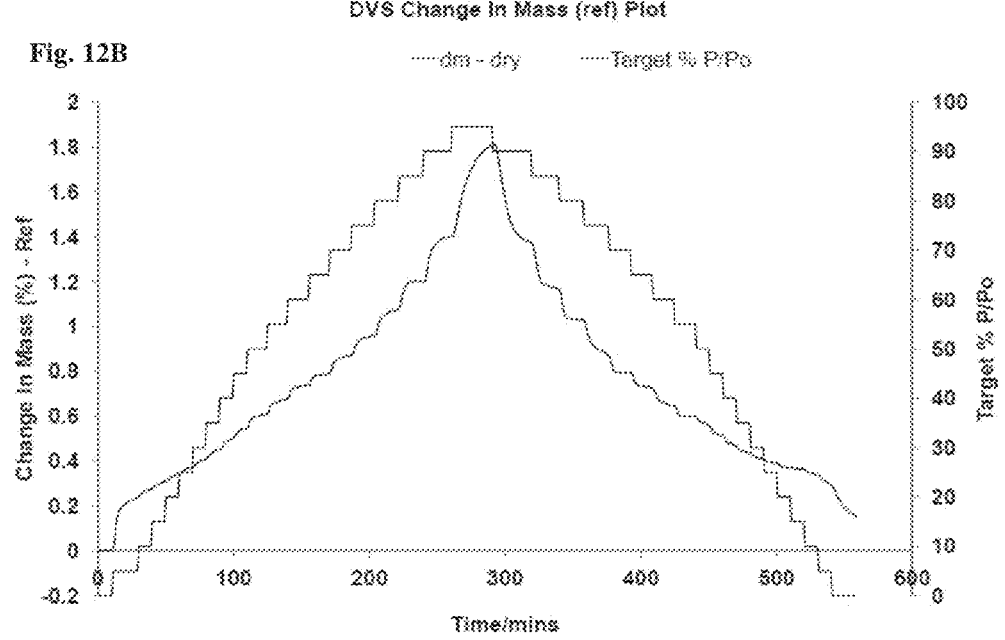

In other embodiments, the dapagliflozin asparagine co-crystal is characterized by a DVS spectrum substantially as shown in FIG. 12. FIG. 12A shows the DVS isotherm plot, and FIG. 12B shows the DVS change in mass.

The present invention further provides a process for the preparation of crystalline dapagliflozin asparagine co-crystal. The process comprises (a) mixing dapagliflozin with asparagine, preferably at about a 1:1 molar ratio in an organic solvent; and (b) precipitating the co-crystal. Any type of organic solvent can be used in this process. Preferred solvents are lower alkyl alcohols (e.g., a $C_1$-$C_6$ alcohol). A currently preferred solvent is isopropanol. Other suitable alcohols include, but are not limited to, methanol, ethanol, propanol, butanol, cyclohexanol and the like.

Any dapagliflozin can be used as the starting material in the process of the present invention, as described above with respect to the lactose co-crystal.

Pharmaceutical Compositions and Therapeutic Methods

The novel dapagliflozin co-crystals of the present invention are useful for the treatment of type 2 diabetes and related conditions such as hyperglycemia. The present invention thus provides pharmaceutical compositions comprising the novel dapagliflozin co-crystal forms disclosed herein and a pharmaceutically acceptable carrier. The pharmaceuticals can be safely administered orally or non-orally. Routes of administration include, but are not limited to, oral, topical, mucosal, nasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural and sublingual. Typically, the dapagliflozin co-crystal forms of the present invention are administered orally. The pharmaceutical compositions can be formulated as tablets (including e.g. film-coated tablets), powders, granules, capsules (including soft capsules), orally disintegrating tablets, and sustained-release preparations as is well known in the art.

Pharmacologically acceptable carriers that may be used in the context of the present invention include various organic or inorganic carriers including, but not limited to, excipients, lubricants, binders, disintegrants, water-soluble polymers and basic inorganic salts. The pharmaceutical compositions of the present invention may further include additives such as, but not limited to, preservatives, antioxidants, coloring agents, sweetening agents, souring agents, bubbling agents and flavorings.

Suitable excipients include e.g. lactose, D-mannitol, starch, cornstarch, crystalline cellulose, light silicic anhydride and titanium oxide. Suitable lubricants include e.g. magnesium stearate, sucrose fatty acid esters, polyethylene glycol, talc and stearic acid. Suitable binders include e.g. hydroxypropyl cellulose, hydroxypropylmethyl cellulose, crystalline cellulose, a-starch, polyvinylpyrrolidone, gum arabic powder, gelatin, pullulan and low-substitutional hydroxypropyl cellulose. Suitable disintegrants include e.g. crosslinked povidone (any crosslinked 1-ethenyl-2-pyrrolidinone homopolymer including polyvinylpyrrolidone (PVPP) and 1-vinyl-2-pyrrolidinone homopolymer), crosslinked carmellose sodium, carmellose calcium, carboxymethyl starch sodium, low-substituted hydroxypropyl cellulose, cornstarch and the like. Suitable water-soluble polymers include e.g. cellulose derivatives such as hydroxypropyl cellulose, polyvinylpyrrolidone, hydroxypropylmethyl cellulose, methyl cellulose and carboxymethyl cellulose sodium, sodium polyacrylate, polyvinyl alcohol, sodium alginate, guar gum and the like.

Suitable preservatives include e.g. sodium benzoate, benzoic acid, and sorbic acid. Suitable antioxidants include e.g. sulfites, ascorbic acid and a-tocopherol. Suitable coloring agents include e.g. food colors such as Food Color Yellow No. 5, Food Color Red No. 2 and Food Color Blue No. 2 and the like. Suitable sweetening agents include e.g. dipotassium glycyrrhetinate, aspartame, stevia and thaumatin. Suitable souring agents include e.g. citric acid (citric anhydride), tartaric acid and malic acid. Suitable bubbling agents include e.g. sodium bicarbonate. Suitable flavorings include synthetic substances or naturally occurring substances, including e.g. lemon, lime, orange, menthol and strawberry.

The dapagliflozin co-crystal forms of the present invention are particularly suitable for oral administration in the form of tablets including sublingual tablet, capsules, pills, dragées, powders, granules, solutions, orally disintegrating wafers, orally disintegrating tablets, and the like. A tablet may be made by compression or molding, optionally with one or more excipients as is known in the art. For example, molded tablets may be made by molding in a suitable machine a mixture of the powdered active ingredient moistened with an inert liquid diluent.

The tablets and other solid dosage forms of the pharmaceutical compositions described herein may optionally be scored or prepared with coatings and shells, such as enteric coatings and other coatings well known in the art. They may also be formulated so as to provide slow or controlled release of the active ingredient therein using, for example, hydroxypropylmethyl cellulose in varying proportions to provide the desired release profile, other polymer matrices and the like. The active ingredient can also be in micro-encapsulated form, if appropriate, with one or more of the above-described excipients.

The present invention provides a method of treating conditions mediated by SLGT2, preferably, type 2 diabetes comprising administering to a subject in need thereof a therapeutically effective amount of a composition comprising any one of the dapagliflozin co-crystals disclosed herein, i.e., the dapagliflozin lactose co-crystal or the dapagliflozin asparagine co-crystal described herein. Each possibility represents a separate embodiment of the present invention.

"A therapeutically effective amount" as used herein refers to an amount of an agent which is effective, upon single or multiple dose administration to the subject in providing a therapeutic benefit to the subject. In one embodiment, the therapeutic benefit is maintaining glucose homeostasis, or regulating blood glucose levels. In additional embodiments, the co-crystal forms of the present invention are used for the preparation of a medicament for treating conditions mediated by SLGT2, preferably type 2 diabetes.

The present invention further provides the administration of the dapagliflozin co-crystals of the present invention in combination therapy with one or more other active ingredients, which are preferably also indicated for the treatment of type 2 diabetes. The combination therapy may include the two or more active ingredients within a single pharmaceutical composition as well as the two or more active ingredients in two separate pharmaceutical compositions administered to the same subject simultaneously or at a time interval determined by a skilled artisan.

The principles of the present invention are demonstrated by means of the following non-limiting examples.

EXAMPLES

Example 1

Materials, Methods and Instruments

1. Reagents
Isopropanol (IPA), HPLC grade, Sigma-Aldrich, Lot No. SHBC4046V
Lactose, AR grade, Aladdin Industrial Corporation, Lot No. H1207032
Asparagine, GL Shanghai Biochem Ltd. Lot. GLS051216-13040
2. Instruments
Balance, CP 225D, Sartorius
Water Purification Equipment, ELGA
Ultrasonicator, KQ-250DB, Kunshan Ultrasonicator Co., Ltd.
Stirrer, C-MAG MS 10, IKA
Polarized Light Microscopy, LV100, Nikon
X-ray diffractometer, D8 Advance, Bruker
DSC, Q2000, TA Instrument
TGA, Q5000, TA Instrument
NMR, AVANCE III 400
Dynamic Vapor Sorption Advantage System, DVS Advantage-1, SMS
3. XRPD, PLM, TGA, MDSC, DSC and DVS Methods
3.1 XRPD Method
Details of XRPD method used in the tests are mentioned below:
  Tube: Cu: K-Alpha ($\lambda$=1.54179 Å).
  Generator: Voltage: 40 kV; Current: 40 mA.
  Detector: PSD: LynxEye.
  Divergence Slit: 0.60 mm; Primary Soller Slit: 2.5 deg.
  Detector Slit: 10.50 mm; Antiscattering Slit: 7.10 mm; Secondary Soller Slit: 2.5 deg.
  Scantype: Locked Coupled; Scan mode: Continuous Scan.
  Scan parameter: Scan axis: 2-Theta/Theta; Scan Scope: 4 to 40 deg; Step size: 0.02 deg; Time/step: 0.12S; Sample rotation speed: 15 rpm.
3.2 Polarized Light Microscope Method
Details of polarized light microscope method used in the tests are mentioned below:
  Nikon LV100 POL equipped with 5 megapixel CCD
  Ocular lens: 10×
  Objective lens: 10× and 20×
  Dispersed medium: silicon oil
3.3 TGA, MDSC and DSC Methods
Details of TGA method used in the tests are mentioned below:
  Heat from 30° C. to 300° C. at 10° C./min
Details of MDSC method used in the tests are mentioned below:
  Heat from 0° C. to 200° C. at 2° C./min
Details of DSC method used in the tests are mentioned below:
  Heat from 25° C. to 300° C. at 10° C./min
3.4 Hygroscopicity Method
Details of DVS method used in the tests are mentioned below:
  Test the sorption/desorption profile of testing compound at 25° C. under 0-95% relative humidity.

Example 2

Preparation and Characterization of Dapagliflozin Lactose and Asparagine Co-Crystals Dapagliflozin free form (45 mg) (designated "Form I"), prepared in accordance with the process of U.S. Pat. No.

6,515,117, was weighed in glass sample vials. The sample was dissolved in 3 ml of IPA. Appropriate amounts of lactose or asparagine were added into a vial individually according to 1:1 molar ratio to dapagliflozin, and then kept under magnetic stirring for 24 hours. The solids precipitated out were isolated. The obtained solids were characterized by XRPD.

In order to confirm the formed solids are co-crystals instead of the precipitated solid co-crystal formers or different polymorphs of dapagliflozin free form, the XRPD diffraction pattern of the formed solid was compared with the solid co-crystal formers (lactose or asparagine), and dapagliflozin Form I. Physical mixtures of dapagliflozin with co-crystal formers were also prepared according to 1:1 molar ratio and characterized by XRPD, PLM and DSC for comparison.

As demonstrated herein, two new co-crystals were formed by these methods, and were designated lactose co-crystal and asparagine co-crystal, respectively. As shown in FIGS. 1A and 7A, these two co-crystals show significantly different XRPD patterns (pattern I (lactose co-crystal) and pattern II (asparagine co-crystal)) as compared with dapagliflozin free form (amorphous), physical mixtures of dapagliflozin with lactose or asparagine and lactose or asparagine alone. Combined with the PLM data, only a crystalline product was observed in the dapagliflozin lactose co-crystal and the dapagliflozin asparagine co-crystal while both crystal and amorphous were observed in physical mixtures. Furthermore, DSC data of lactose co-crystal and asparagine co-crystal also show some difference from its respective physical mixtures, thus further confirming that these are new co-crystallized forms of dapagliflozin with lactose or asparagine.

The preparation of lactose co-crystal and asparagine co-crystal were scaled up and repeated (about 400 mg of dapagliflozin free form was dissolved in 26 ml of IPA) and XRPD, PLM, TGA, DSC, NMR and DVS analyses were conducted for physicochemical properties evaluation. Before physicochemical properties evaluation, the solids precipitated out were isolated and dried off at 40° C. for 4 hours in vacuum drier. After hygroscopicity test, the sample was retested by XRPD to determine if any form transformation during the DVS test.

The results are shown in FIGS. 2-6 and 8-12. FIG. 2 illustrates the DSC profile of the dapagliflozin lactose co-crystal. FIG. 3A illustrates the PLM profile of the dapagliflozin lactose co-crystal. Shown in comparison (FIG. 3B) is a physical mixture of dapagliflozin and lactose. FIG. 4 illustrates the TGA profile of the dapagliflozin lactose co-crystal. FIG. 5 illustrates the $^1$H-NMR profile of the dapagliflozin lactose co-crystal. FIG. 6 illustrates the DVS profile of the dapagliflozin lactose co-crystal (data also shown in Table 1). FIG. 8 illustrates the DSC profile of the dapagliflozin asparagine co-crystal. FIG. 9A illustrates the PLM profile of the dapagliflozin asparagine co-crystal. Shown in comparison (FIG. 9B) is a physical mixture of dapagliflozin and asparagine. FIG. 10 illustrates the TGA profile of the dapagliflozin asparagine co-crystal. FIG. 11 illustrates the $^1$H-NMR profile of the dapagliflozin asparagine co-crystal. FIG. 12 illustrates the DVS profile of the dapagliflozin asparagine co-crystal (data also shown in Table 2).

As per the TGA and DSC profiles (FIGS. 2, 4, 8 and 10), the melting point of the lactose co-crystal is about 228° C. and this forms begins to decompose simultaneously when melting. The melting point of asparagine co-crystal is about 228° C. and this form also begins to decompose simultaneously when melting.

Figure 7B:
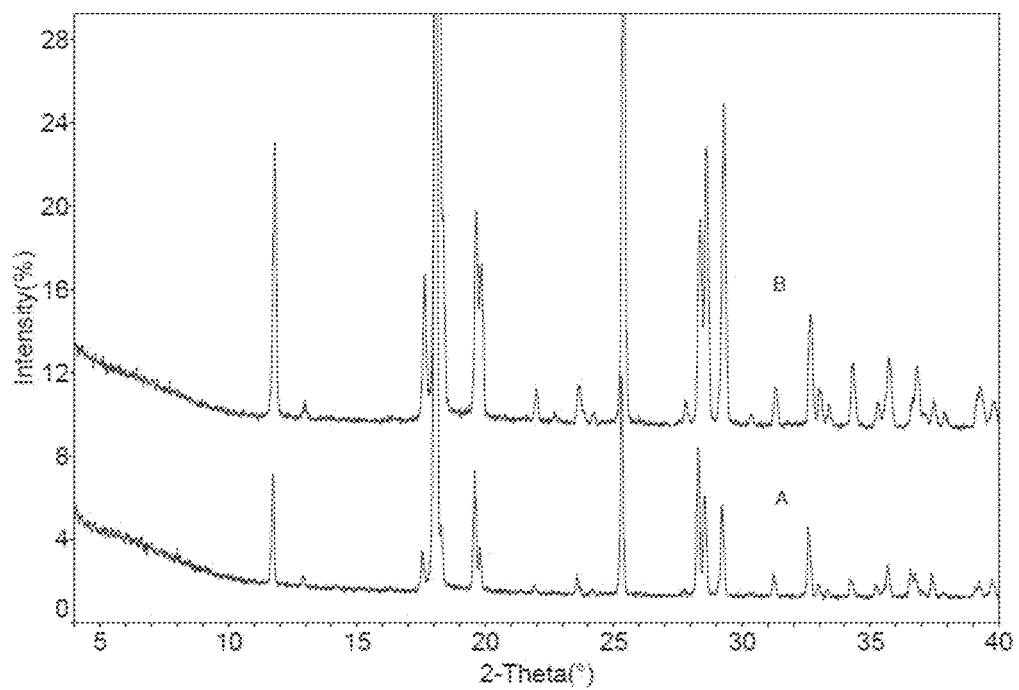

Based on the DVS data (FIGS. 6 and 12) and Tables 1 and 2, the lactose co-crystal could be classified as hygroscopic (2.16% weight gain from 0 to 95% RH) and the asparagine co-crystal could be classified as slightly hygroscopic (1.80% weight gain from 0 to 95% RH) according to the following definitions. As per the XRPD result after DVS test (FIGS. 1B and 7B), no form transformation was found for the two co-crystals.

Hygroscopicity Definitions

Deliquescent: Sufficient water is absorbed to form a liquid.

Very hygroscopic: Increase in mass is equal to or greater than 15%.

Hygroscopic: Increase in mass is equal to or greater than 2%, but less than 15%.

Slightly hygroscopic: Increase in mass is less than 2% and equal to or greater than 0.2%, but less than 2%.

Non-hygroscopic: Increase in mass is less than 0.2%.

TABLE 1

DVS Isotherm Data (lactose co-crystal).

| Target | Change In Mass (%) - ref | | |
|---|---|---|---|
| % P/Po | Sorption | Desorption | Hysteresis |

| | | | | |
|---|---|---|---|---|
| Cycle 1 | 0.0 | 0.000 | 0.077 | |
| | 5.0 | 0.021 | 0.104 | 0.083 |
| | 10.0 | 0.042 | 0.120 | 0.078 |
| | 15.0 | 0.064 | 0.136 | 0.073 |
| | 20.0 | 0.085 | 0.151 | 0.066 |
| | 25.0 | 0.107 | 0.170 | 0.063 |
| | 30.0 | 0.131 | 0.188 | 0.058 |
| | 35.0 | 0.160 | 0.213 | 0.053 |
| | 40.0 | 0.201 | 0.238 | 0.036 |
| | 45.0 | 0.244 | 0.266 | 0.022 |
| | 50.0 | 0.283 | 0.296 | 0.013 |
| | 55.0 | 0.323 | 0.330 | 0.007 |
| | 60.0 | 0.363 | 0.366 | 0.003 |
| | 65.0 | 0.409 | 0.410 | 0.000 |
| | 70.0 | 0.466 | 0.465 | 0.000 |
| | 75.0 | 0.534 | 0.531 | −0.004 |
| | 80.0 | 0.622 | 0.618 | −0.004 |
| | 85.0 | 0.762 | 0.768 | 0.005 |
| | 90.0 | 1.012 | 1.081 | 0.069 |
| | 95.0 | 2.162 | 2.162 | |

TABLE 2

DVS Isotherm Data (Asparagine co-crystal)

| Target | Change In Mass (%) - ref | | |
|---|---|---|---|
| % P/Po | Sorption | Desorption | Hysteresis |

| | | | | |
|---|---|---|---|---|
| Cycle 1 | 0.0 | 0.002 | 0.159 | |
| | 5.0 | 0.231 | 0.302 | 0.071 |
| | 10.0 | 0.270 | 0.341 | 0.071 |
| | 15.0 | 0.304 | 0.364 | 0.060 |
| | 20.0 | 0.336 | 0.371 | 0.035 |
| | 25.0 | 0.370 | 0.392 | 0.022 |
| | 30.0 | 0.404 | 0.412 | 0.009 |
| | 35.0 | 0.446 | 0.440 | −0.006 |
| | 40.0 | 0.493 | 0.474 | −0.020 |
| | 45.0 | 0.542 | 0.517 | −0.026 |
| | 50.0 | 0.607 | 0.565 | −0.042 |
| | 55.0 | 0.673 | 0.600 | −0.073 |
| | 60.0 | 0.736 | 0.650 | −0.086 |
| | 65.0 | 0.786 | 0.729 | −0.057 |
| | 70.0 | 0.869 | 0.794 | −0.075 |
| | 75.0 | 0.956 | 0.878 | −0.078 |
| | 80.0 | 1.072 | 1.031 | −0.041 |
| | 85.0 | 1.201 | 1.171 | −0.030 |
| | 90.0 | 1.397 | 1.378 | −0.019 |
| | 95.0 | 1.798 | 1.798 | |

Conclusion

Two co-crystals were of dapagliflozin formed—a lactose co-crystal and an asparagine co-crystal. These two co-crystals were further characterized by XRPD, DSC, TGA, PLM, DVS and NMR.

Comparative Example 3

Dapagliflozin Form I

1. Characterization of Dapagliflozin Form I

Figure 13:
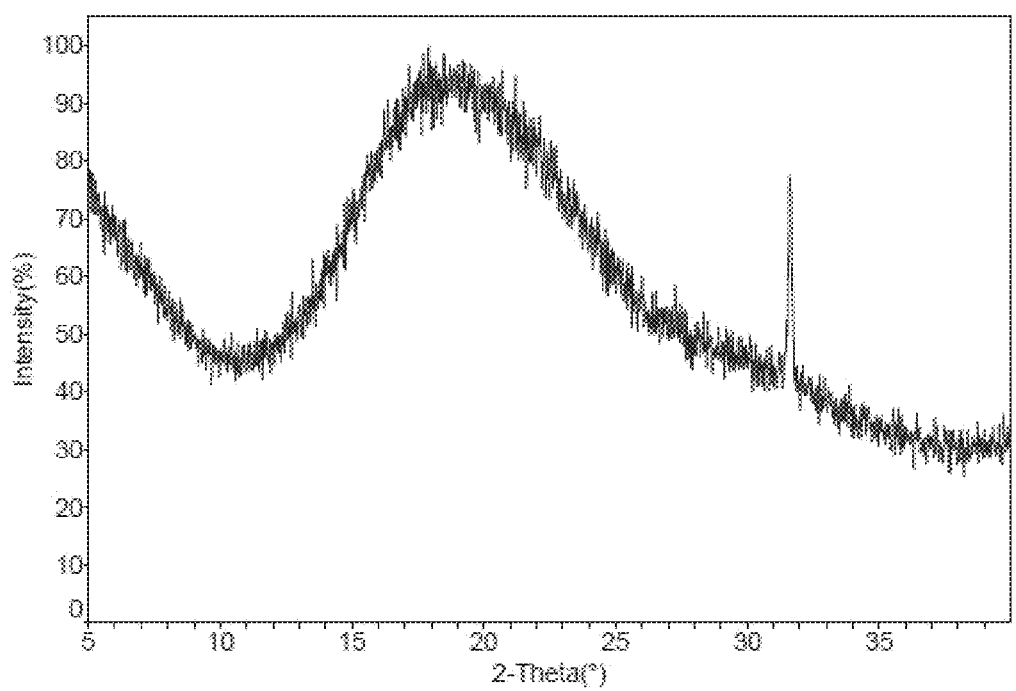
FIG. 13 illustrates a characteristic X-ray diffraction pattern of a dapagliflozin free form (amorphous).
Figure 14:
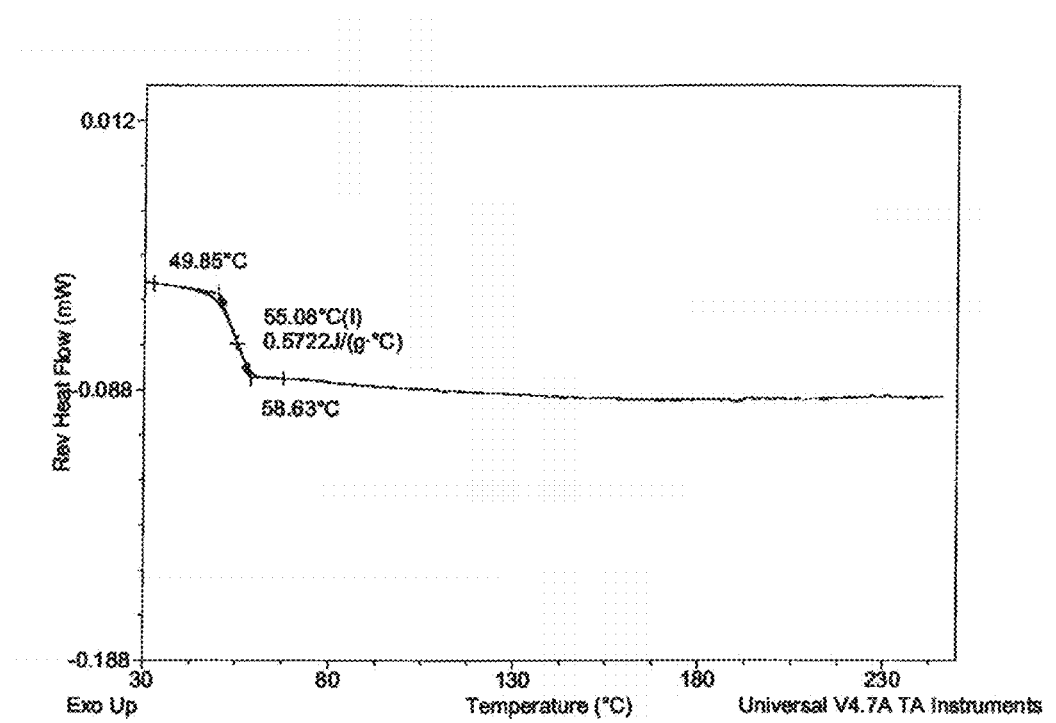
FIG. 14 illustrates a characteristic Modulated Differential Scanning Calorimetry (MDSC) profile of a dapagliflozin free form (amorphous).
Figure 15:
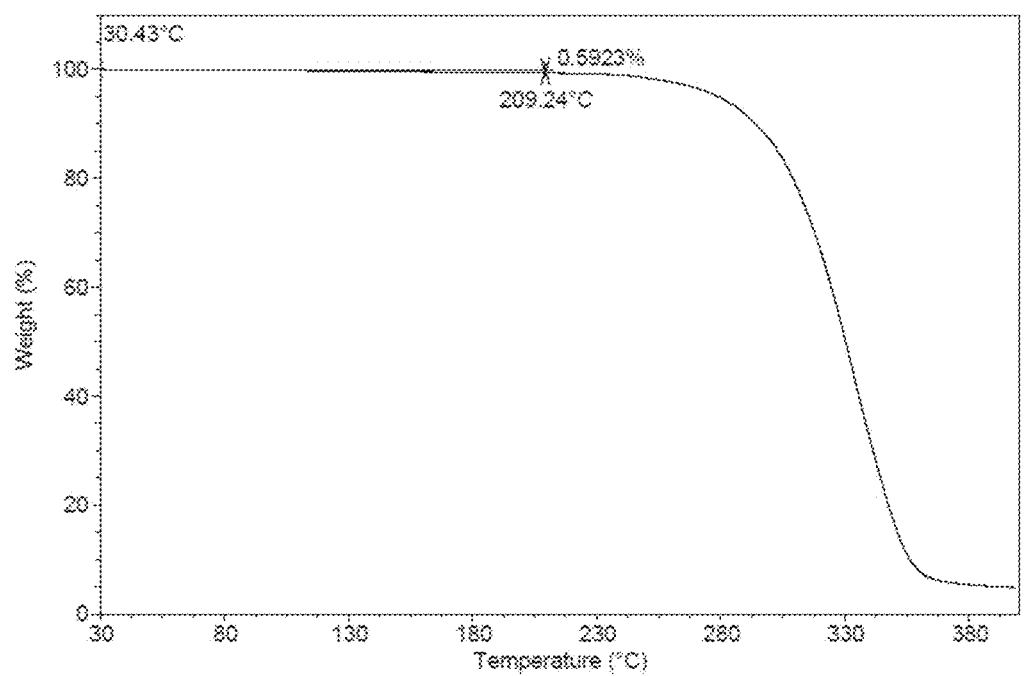
FIG. 15 illustrates a characteristic TGA profile of a dapagliflozin free form (amorphous).
Figure 16:
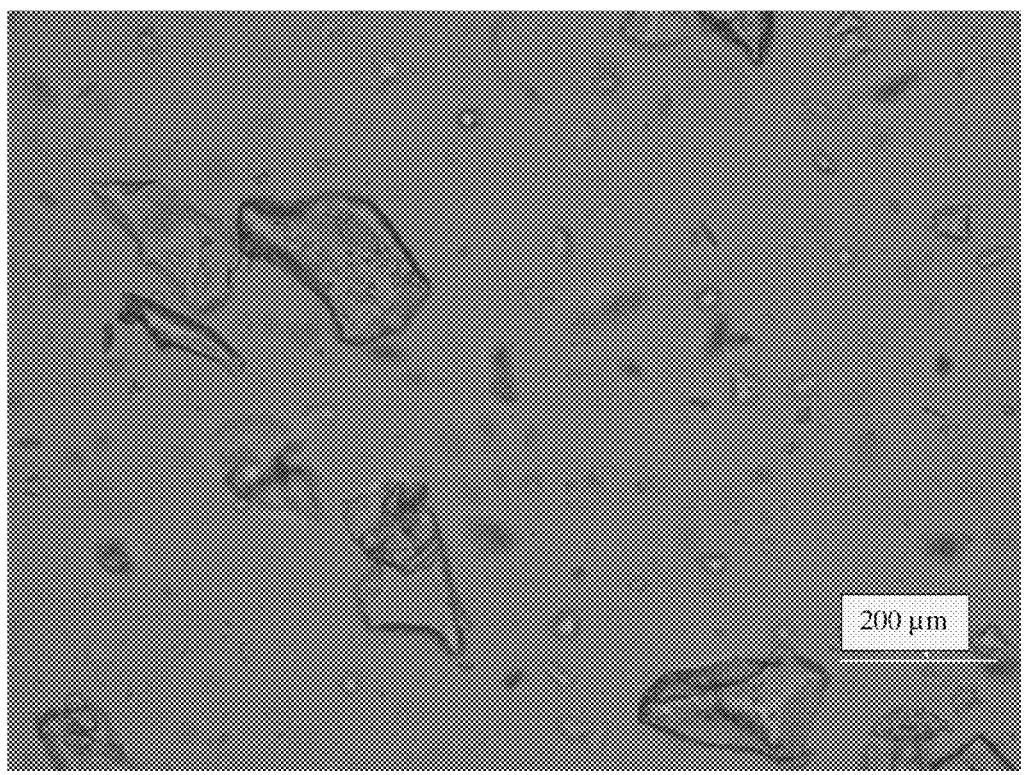
FIG. 16 illustrates a characteristic PLM spectrum of a dapagliflozin free form (amorphous) (10×PL).
Figure 17:
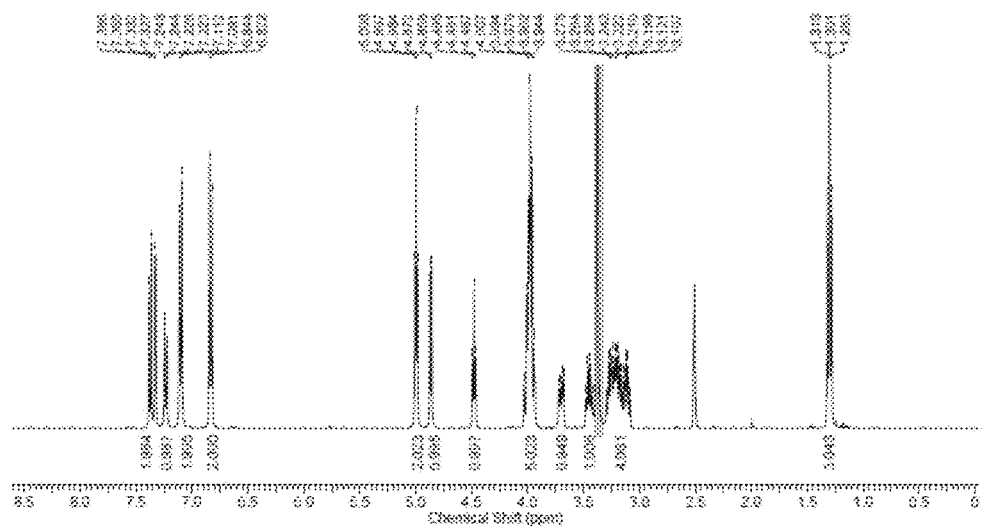
FIG. 17 illustrates a characteristic $^1$H-NMR spectrum of a dapagliflozin free form (amorphous).

Dapagliflozin Form I was prepared in accordance with the method described in U.S. Pat. No. 6,515,117, and was characterized by XRPD, MDSC, TGA, and Microscopy (the sample was dispersed in silicon oil on a glass slide without cover slip). The results are listed in FIG. 13 to FIG. 17. FIG. 13 illustrates a characteristic XRPD pattern of dapagliflozin Form I. FIG. 14 illustrates a characteristic MDSC profile of dapagliflozin Form I. FIG. 15 illustrates a characteristic TGA profile of dapagliflozin Form I. FIG. 16 illustrates a characteristic PLM profile of dapagliflozin Form I. FIG. 17 illustrates a characteristic $^1$H-NMR profile of dapagliflozin Form I. As per the results, Form I is amorphous, and the glass transition temperature is 55.08° C. It is likely that some inorganic impurities show the 32 deg peak in its XRPD profile.

2. Characterization of Dapagliflozin Form 1 at 1.5 Months

Dapagliflozin was stored at −20° C., tightly closed. After being stored for 1.5 month, it was characterized by XRPD, MDSC and TGA to check if it is stable. As per the results, no form transformation was detected. It is stable at this store condition (−20° C., tightly closed) for 1.5 month (data not shown).

3. Hygroscopicity of Dapagliflozin Form I.

Figure 18A:
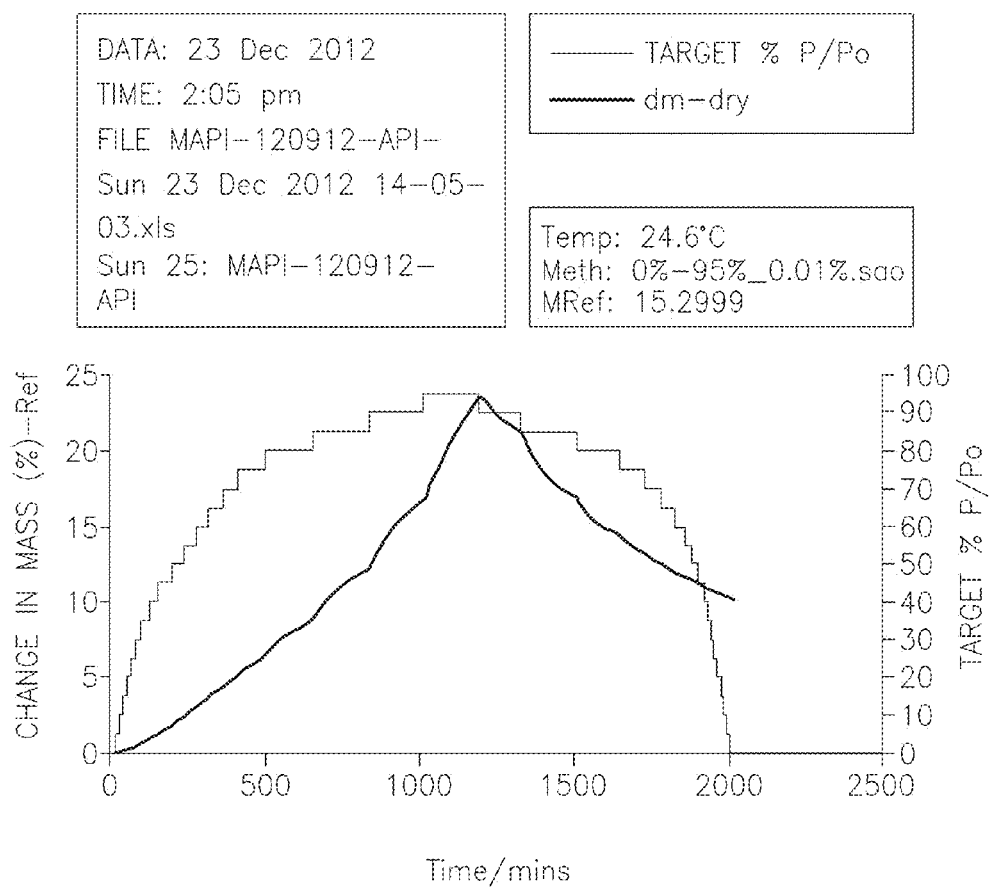
FIGS. 18A and 18B illustrate a characteristic DVS spectrum of a dapagliflozin free form (amorphous).
Figure 18B:
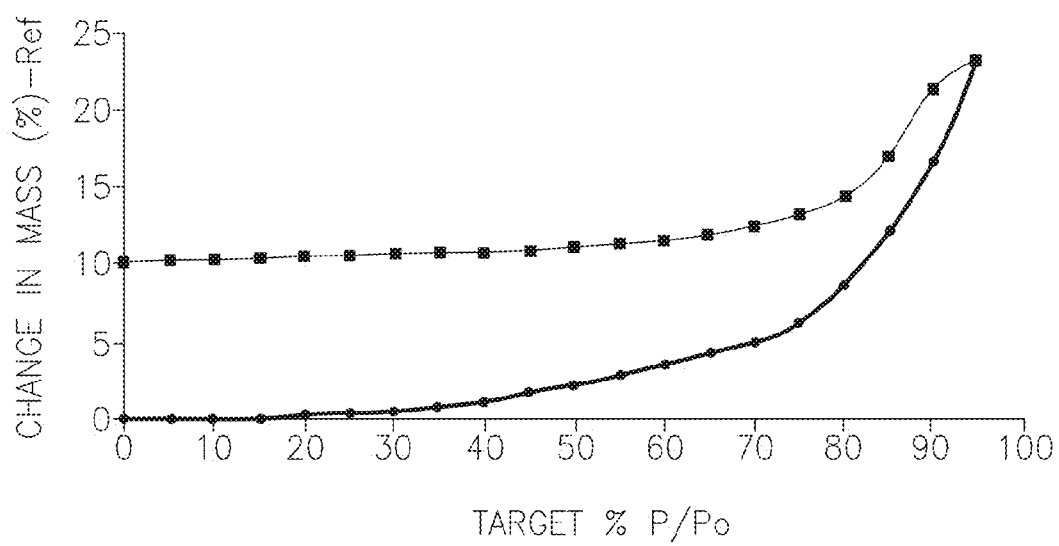
Figure 19:
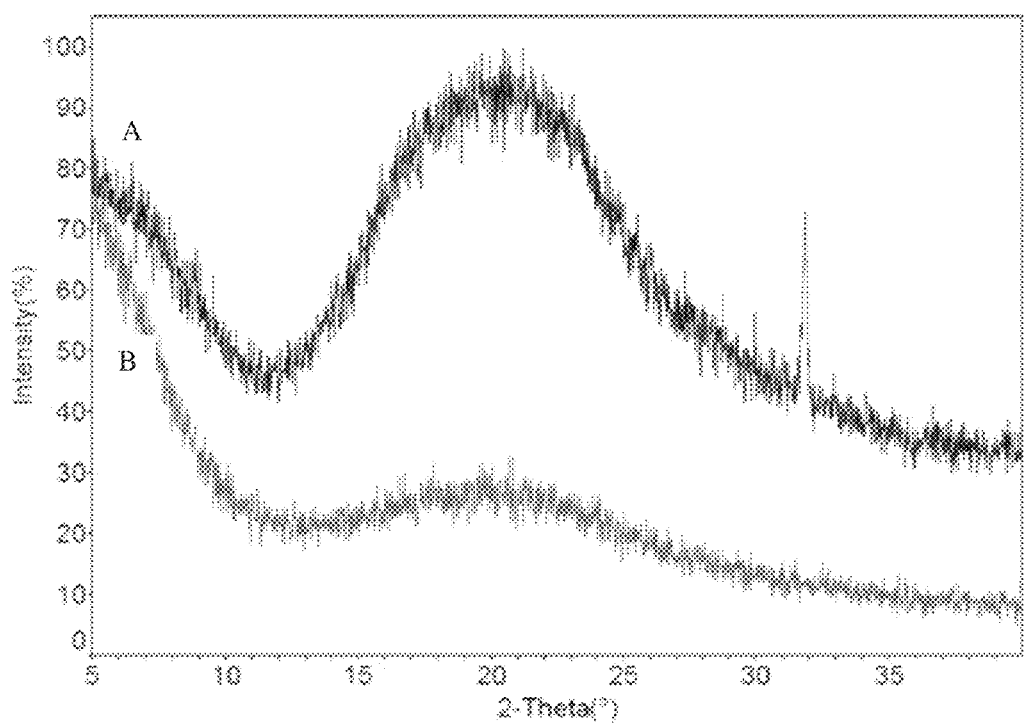
FIG. 19 illustrates a characteristic X-ray diffraction pattern of a dapagliflozin free form (amorphous), before (A) and after (B) DVS test.

The sorption/desorption profiles of dapagliflozin Form I were tested at 25° C. under 0-95% relative humidity. The sample after testing DVS had become thick gel-like material. This sample was tested by XRPD. The results are shown in FIGS. 18 and 19 and in Table 3. As per the DVS results (FIG. 18 and Table 3), dapagliflozin could be classified as very hygroscopic (23.33% % weight gain from 0 to 95% RH) according to the criteria defined in Example 2. As per the XRPD result, the amorphous was found after testing DVS. These results indicate that the amorphous is formed by water absorption of the API.

TABLE 3

DVS Isotherm Data (Form I)

| Target | Change In Mass (%) - ref | | |
|---|---|---|---|
| % P/Po | Sorption | Desorption | Hysteresis |
| Cycle 1  0.0 | 0.00 | 10.18 | |
| 5.0 | 0.09 | 10.26 | 10.18 |
| 10.0 | 0.14 | 10.34 | 10.20 |
| 15.0 | 0.23 | 10.42 | 10.19 |
| 20.0 | 0.30 | 10.50 | 10.20 |
| 25.0 | 0.41 | 10.58 | 10.16 |
| 30.0 | 0.55 | 10.66 | 10.10 |
| 35.0 | 0.83 | 10.74 | 9.91 |
| 40.0 | 1.18 | 10.83 | 9.65 |
| 45.0 | 1.75 | 10.97 | 9.22 |
| 50.0 | 2.31 | 11.15 | 8.85 |
| 55.0 | 2.89 | 11.35 | 8.46 |
| 60.0 | 3.54 | 11.59 | 8.05 |
| 65.0 | 4.27 | 11.95 | 7.67 |
| 70.0 | 4.94 | 12.47 | 7.53 |
| 75.0 | 6.21 | 13.23 | 7.02 |
| 80.0 | 8.73 | 14.44 | 5.71 |
| 85.0 | 12.09 | 16.99 | 4.90 |
| 90.0 | 16.70 | 21.36 | 4.66 |
| 95.0 | 23.33 | 23.33 | |

Conclusion

Based on the characterization of Form I (original form), it is amorphous, and the glass transition temperature is 55.08° C. It is likely that some inorganic impurities show the 32 deg peak in its XRPD profile. Form I is stable after storing at −20° C., tightly closed for 1.5 month.

Based on the DVS data, Form I is very hygroscopic (23.33% % weight gain from 0 to 95% RH). It became a thick gel after DVS testing, and an amorphous form (not containing the 32 deg peak) was detected in its XRPD profile. It was also observed that Form I absorbed moisture from air or solvents to form gel-like consistency.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A co-crystal of dapagliflozin with lactose.

Figure 1B:
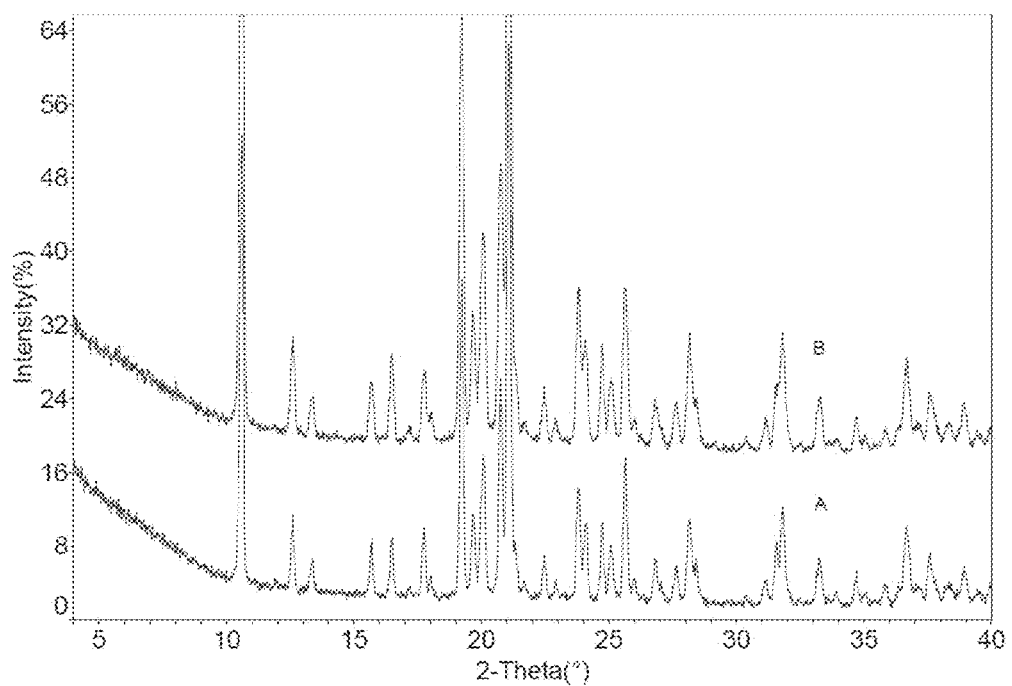

2. The dapagliflozin lactose co-crystal according to claim 1, characterized by an X-ray powder diffraction (XRPD) pattern substantially as shown in FIG. 1A or 1B.

3. The dapagliflozin lactose co-crystal according to claim 1, further characterized by a Differential Scanning Calorimetry (DSC) profile substantially as shown in FIG. 2.

4. The dapagliflozin lactose co-crystal according to claim 1, further characterized by a Polarized Light Microscope (PLM) profile substantially as shown in FIG. 3A.

5. The dapagliflozin lactose co-crystal according to claim 1, further characterized by a Thermogravimetric Analysis (TGA) profile substantially as shown in FIG. 4.

6. The dapagliflozin lactose co-crystal according to claim 1, further characterized by a $^1$H-NMR profile substantially as shown in FIG. 5.

7. The dapagliflozin lactose co-crystal according to claim 1, further characterized by a Dynamic Vapor Sorption (DVS) profile substantially as shown in FIG. 6A and 6B.

8. A pharmaceutical composition comprising as an active ingredient the crystalline dapagliflozin lactose co-crystal according to claim 1, and a pharmaceutically acceptable carrier.

9. The pharmaceutical composition according to claim 8, in the form of a tablet, a capsule, a pill, a powder or a solution.

10. A method of treating a condition mediated by the sodium dependent glucose transporter (SGLT2), comprising administering to a subject in need thereof an effective amount of a dapagliflozin lactose co-crystal according to claim 1, or a pharmaceutical composition comprising said co-crystal, to effectuate such treatment.

11. The method according to claim 10, wherein the condition mediated by SGLT2 is type 2 diabetes.

12. The method according to claim 10, wherein the subject is a human.

13. A process for preparing the dapagliflozin lactose co-crystal according to claim 1, the process comprising the steps of mixing dapagliflozin with lactose in an organic solvent, wherein the organic solvent is a $C_1$-$C_6$ alcohol, and precipitating the co-crystal.

14. The process according to claim 13, wherein the dapagliflozin and lactose are mixed at a 1:1 molar ratio.

15. The process according to claim 13, wherein the organic solvent is isopropanol.

\* \* \* \* \*